United States Patent
Sarely et al.

(10) Patent No.: US 11,925,446 B2
(45) Date of Patent: Mar. 12, 2024

(54) RADAR-BASED CLASSIFICATION OF VEHICLE OCCUPANTS

(71) Applicant: VAYYAR IMAGING LTD., Yehud (IL)

(72) Inventors: Mariana Sarely, Netanya (IL); Robin Olschewski, Ramat Gan (IL); Tsachi Rosenhouse, Kiryat Ono (IL)

(*) Notice: Subject to any disclaimer, the term of this patent is extended or adjusted under 35 U.S.C. 154(b) by 256 days.

(21) Appl. No.: 17/033,801

(22) Filed: Sep. 27, 2020

(65) Prior Publication Data
US 2021/0052176 A1 Feb. 25, 2021

Related U.S. Application Data

(63) Continuation-in-part of application No. 16/983,004, filed on Aug. 3, 2020, now Pat. No. 11,033,194, which is a continuation of application No. 16/282,650, filed on Feb. 22, 2019, now Pat. No. 10,729,339.

(60) Provisional application No. 63/056,629, filed on Jul. 26, 2020, provisional application No. 62/906,182, filed on Sep. 26, 2019, provisional application No. 62/689,260, filed on Jun. 25, 2018, provisional application No. 62/633,676, filed on Feb. 22, 2018.

(51) Int. Cl.
*A61B 5/024* (2006.01)
*A61B 5/08* (2006.01)
*G01S 7/41* (2006.01)
*G01S 13/42* (2006.01)

(52) U.S. Cl.
CPC ...... *A61B 5/02444* (2013.01); *A61B 5/02405* (2013.01); *A61B 5/0816* (2013.01); *G01S 7/41* (2013.01); *G01S 13/42* (2013.01)

(58) Field of Classification Search
CPC ............ A61B 5/02444; A61B 5/02405; A61B 5/0816; G01S 7/41; G01S 13/42
USPC .......................................................... 342/22
See application file for complete search history.

(56) References Cited

U.S. PATENT DOCUMENTS

| | | | | |
|---|---|---|---|---|
| 6,772,057 B2* | 8/2004 | Breed | ..................... | B60N 2/002 280/735 |
| 6,961,443 B2* | 11/2005 | Mahbub | ............ | B60R 21/01538 382/104 |
| 7,245,741 B1* | 7/2007 | Ertl | ..................... | B60R 21/01538 180/277 |
| 7,415,126 B2* | 8/2008 | Breed | ............... | B60R 21/01552 701/44 |
| 7,655,895 B2* | 2/2010 | Breed | .................. | B60R 21/0152 250/221 |
| 7,831,358 B2* | 11/2010 | Breed | ............... | B60R 21/01542 385/33 |
| 8,152,198 B2* | 4/2012 | Breed | ............... | B60R 21/01516 701/45 |
| 9,123,186 B2* | 9/2015 | Ricci | ..................... | H04W 4/21 |
| 10,991,242 B2* | 4/2021 | Taylor | ..................... | H04Q 9/00 |

(Continued)

*Primary Examiner* — Nuzhat Pervin
(74) *Attorney, Agent, or Firm* — AlphaPatent Associates Ltd.; Daniel J. Swirsky

(57) ABSTRACT

Using transmitters and receivers for detecting occupants in a vehicle, and classifying those occupants according to the geometry of the vehicle, where sets of complex values associated with voxels in a predetermined region of the vehicle are converted into 3D complex images, where clusters of voxels in the 3D complex images are analyzed to determine presence of occupants, and where positions of seats may determine which seats in the vehicle are occupied.

20 Claims, 26 Drawing Sheets

(56) References Cited

U.S. PATENT DOCUMENTS

| | | | | |
|---|---|---|---|---|
| 11,230,293 B2* | 1/2022 | Gomez | ................... | G01S 7/414 |
| 11,269,891 B2* | 3/2022 | Frank | ................... | G06F 16/904 |
| 2001/0003168 A1* | 6/2001 | Breed | ................... | G06V 40/10 |
| | | | | 701/45 |
| 2002/0029103 A1* | 3/2002 | Breed | ................... | B60N 2/0244 |
| | | | | 701/45 |
| 2002/0050924 A1* | 5/2002 | Mahbub | ................... | G01S 17/89 |
| | | | | 340/426.1 |
| 2002/0082756 A1* | 6/2002 | Breed | ............... | B60R 21/01516 |
| | | | | 701/45 |
| 2002/0116106 A1* | 8/2002 | Breed | ................... | B60R 21/013 |
| | | | | 348/148 |
| 2003/0169906 A1* | 9/2003 | Gokturk | ................. | G06V 20/59 |
| | | | | 382/190 |
| 2003/0209893 A1* | 11/2003 | Breed | ............... | B60R 21/01554 |
| | | | | 701/45 |
| 2004/0129478 A1* | 7/2004 | Breed | ................... | B60R 22/20 |
| | | | | 180/273 |
| 2004/0186642 A1* | 9/2004 | Basir | ................... | G06V 40/10 |
| | | | | 701/45 |
| 2005/0131607 A1* | 6/2005 | Breed | ................... | B60R 25/255 |
| | | | | 701/45 |
| 2006/0214835 A1* | 9/2006 | Lee | ................... | G01V 8/005 |
| | | | | 342/25 R |
| 2007/0154063 A1* | 7/2007 | Breed | ............... | B60R 21/01538 |
| | | | | 382/100 |
| 2007/0282506 A1* | 12/2007 | Breed | ................... | B60N 2/028 |
| | | | | 701/45 |
| 2008/0051957 A1* | 2/2008 | Breed | ................... | G06V 20/593 |
| | | | | 701/36 |
| 2008/0065291 A1* | 3/2008 | Breed | ................... | G08B 21/22 |
| | | | | 382/190 |
| 2008/0069403 A1* | 3/2008 | Breed | ................... | B60K 28/066 |
| | | | | 382/104 |
| 2008/0217472 A1* | 9/2008 | Diamandis | ........... | B64D 27/023 |
| | | | | 244/1 R |
| 2008/0294315 A1* | 11/2008 | Breed | ................... | G06V 20/584 |
| | | | | 701/49 |
| 2009/0066065 A1* | 3/2009 | Breed | ................... | B60R 21/0152 |
| | | | | 340/573.1 |
| 2009/0092284 A1* | 4/2009 | Breed | ................... | B60R 21/0153 |
| | | | | 382/103 |
| 2010/0096491 A1* | 4/2010 | Whitelaw | ................. | B64G 1/00 |
| | | | | 725/75 |
| 2011/0285982 A1* | 11/2011 | Breed | ................... | G06V 20/59 |
| | | | | 356/614 |
| 2012/0106821 A1* | 5/2012 | Madabhushi | ........ | G06V 10/764 |
| | | | | 382/133 |
| 2012/0319870 A1* | 12/2012 | Riedel | ................... | G02B 30/26 |
| | | | | 340/945 |
| 2013/0001422 A1* | 1/2013 | Lavon | ................... | G01S 13/42 |
| | | | | 250/393 |
| 2014/0097957 A1* | 4/2014 | Breed | ................... | G08B 21/06 |
| | | | | 340/576 |
| 2014/0201126 A1* | 7/2014 | Zadeh | ................... | A61B 5/165 |
| | | | | 706/52 |
| 2015/0301167 A1* | 10/2015 | Sentelle | ............... | A61B 5/0205 |
| | | | | 342/22 |
| 2016/0104290 A1* | 4/2016 | Patnaik | ................. | G01V 5/0016 |
| | | | | 382/173 |
| 2016/0170998 A1* | 6/2016 | Frank | ................... | G06F 16/908 |
| | | | | 707/748 |
| 2016/0361041 A1* | 12/2016 | Barsimantov | .......... | A61B 8/065 |
| 2017/0315225 A1* | 11/2017 | Lee | ................... | G01S 13/585 |
| 2018/0067490 A1* | 3/2018 | Pollach | ................. | G05D 1/0255 |
| 2018/0128915 A1* | 5/2018 | Lomnitz | ................ | G01S 13/9029 |
| 2018/0143311 A1* | 5/2018 | Melamed | ................ | G01S 13/89 |
| 2018/0204111 A1* | 7/2018 | Zadeh | ................... | G06V 10/764 |
| 2018/0299543 A1* | 10/2018 | Lomnitz | ................ | G01S 7/025 |
| 2019/0164018 A1* | 5/2019 | Zhu | ................... | G05D 1/0248 |
| 2019/0188541 A1* | 6/2019 | Wang | ................... | G01S 7/4802 |
| 2019/0333233 A1* | 10/2019 | Hu | ................... | G01S 13/04 |
| 2020/0138381 A1* | 5/2020 | LeBoeuf | ............ | A61B 5/02108 |
| 2020/0331146 A1* | 10/2020 | Vu | ................... | G06T 19/20 |
| 2020/0331155 A1* | 10/2020 | Vu | ................... | B25J 19/06 |
| 2022/0121884 A1* | 4/2022 | Zadeh | ................... | G06V 10/764 |

* cited by examiner

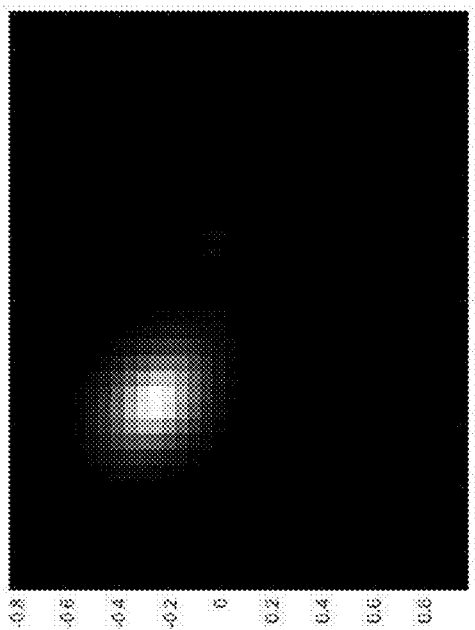
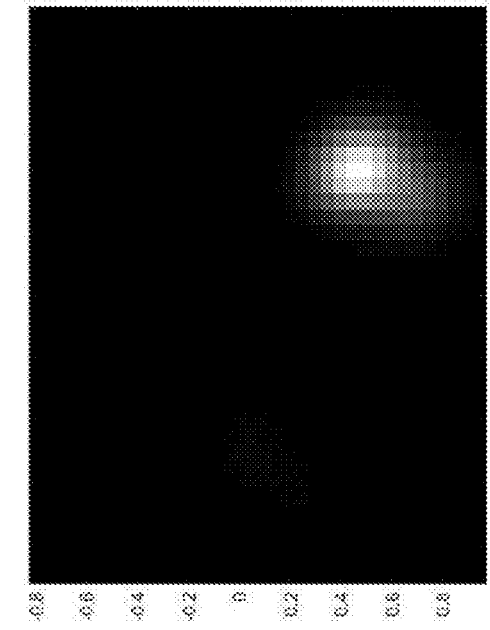
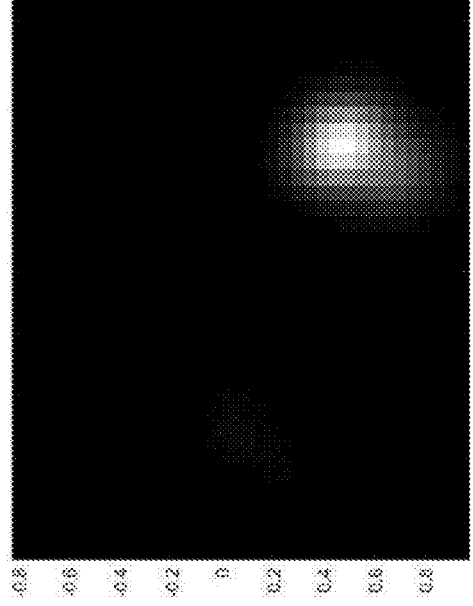
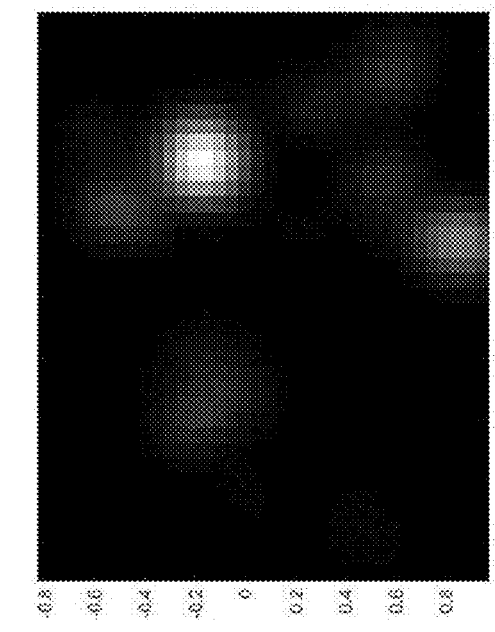
Fig. 8a
Fig. 8b
Fig. 8c
Fig. 8d

RADAR-BASED CLASSIFICATION OF VEHICLE OCCUPANTS

CROSS-REFERENCE TO RELATED APPLICATIONS

This application is a Continuation-In-Part of U.S. patent application Ser. No. 16/983,004 which was filed on Aug. 3, 2020, as a continuation of U.S. patent application Ser. No. 16/282,650 which was filed on Feb. 22, 2019, and which, in turn, claims priority and benefit from U.S. Provisional Patent Application No. 62/633,676, filed Feb. 22, 2018, and U.S. Provisional Patent Application No. 62/689,260, filed Jun. 25, 2018. This application further claims priority and benefit from U.S. Provisional Patent Application No. 62/906,782, filed Sep. 26, 2019 and U.S. Provisional Patent Application No. 63/056,629, filed Jul. 26, 2020. The contents and disclosures of the above-identified applications are incorporated herein by reference in their entirety.

FIELD

The disclosure herein relates to systems and methods for classifying occupants of vehicles. In some embodiments thereof, the disclosure relates to classifying of one or more objects in a vehicle based on radar measurements, and more specifically, but not exclusively, to determine the mass or size of occupying objects in a vehicle and controlling the vehicle's system such as the vehicle's airbag system based on the measured mass or size of the occupying object.

BACKGROUND

It is important to know how many occupants there are in a vehicle and where they are sitting.

For various reasons it is useful to know whether seats of a vehicle are occupied.

Embodiments of the Modern vehicles include a plethora of sensors for determining the occupancy of a vehicle. These include sensors for identifying whether each seat is occupied, whether a baby is in a front seat so as to disable airbags and so on.

There is a limit to the number of passengers that a vehicle is allowed to carry. There are also size and weight limitations regarding different seats of the vehicle. passengers under a certain age are not allowed to sit in front seats, for example.

In some jurisdictions, to encourage carpooling, private vehicles are allowed to use preferential roads such as bus-lanes if they are carrying at least a specific number of passengers in addition to the driver.

Wideband MIMO radar apparatus based on compact antenna arrays is currently used in various imaging applications to visualize near-field as well as far-field objects and characterize them based on their reflective properties.

Current state of the art techniques use MIMO radar signal to create 3D images. However, current MIMO imaging techniques lack the ability to achieve adequate resolvability when identifying targets in close proximity to each other or are found in a moving environment.

Complex target objects having different parts, each having their own mode of movement further complicate imaging with sufficient resolvability. Therefore, there is need to advance current MIMO radar imaging techniques to achieve a higher degree of resolvability.

Having a large number of sensors monitoring the inside of a vehicle causes expense and reliability issues. There is a need to obtain the same information with a simpler system. The disclosure addresses this need.

SUMMARY

It is an aspect of the current embodiment to teach a method for detecting occupants in a vehicle using transmitters and receivers and classifying those occupants according to the detected signals.

Accordingly, methods may include, for each of a plurality of times, using an array of transmitting and receiving elements to generate a set of complex values associated with voxels in a predetermined region of the vehicle; converting each set of complex values into a 3D complex image; clustering the voxels in the 3D complex images into one or more clusters; analyzing the clusters to determine presence of one or more occupants inside the vehicle; and using geometrical data of the vehicle regarding the position of seats to determine which seats in the vehicle are occupied.

Variously, the array of transmitting and receiving elements may be radar imaging or ultrasonic imaging elements or the like. In particular the array of transmitting and receiving elements may use radiation having a wavelength from 0.1 cm to 10 cm.

Where appropriate, the method may include steps of background removal prior to the step of clustering, and filtering one or more images prior to the step of clustering. If the filtering step leaves components as associated with at least two separate clusters, a DBSCAN algorithm may be used to associate components with a single cluster.

Optionally, a clustering algorithm is applied to each cluster which is represented as a Gaussian distribution with mean and covariance which fit the distribution of points within the cluster and applying distance metrics between the Gaussian distributions. For example, the distance metric between Gaussian distributions utilizes at least one of Kullback Leibler divergence, Bhattacharyya distance, Hellinger distance and L2-norm of the difference. Optionally, a spectral clustering algorithm is used to distance different distributions. It is noted that a cluster of points may be defined by a technique selected from t-distribution, uniform distribution or a Gaussian mixture.

In some examples, extreme voxels of a cluster determine a box around an occupant that may be used to categorize the occupant. Accordingly, the relative position of a center of intensity of a cluster of voxels with respect to a seat back is used as an indication that an occupant is leaning forwards or backwards. For example, a cluster lacking voxels below seat level may be indicative of an infant.

In accordance with another embodiment of the present invention there is provided a method for classifying one or more occupants in a vehicle cabin comprising one or more seats, the method comprising: providing a processor configured to: obtain one or more 3D (three dimensional) images;

process one or more consecutive 3D images of said obtained 3D images, said processing comprises:

remove background of said one or more consecutive 3D images; filter said one or more consecutive 3D images, said filtering comprises removing contribution of one or more of: sidelobes, multipath, thermal noise and cutter; cluster said filtered 3D images; associate one of the one or more seats to said one or more occupants and classify the one or more occupants based on feature computation said feature computation comprises: distribution of points for each cluster in said 3D images and according to said vehicle geometry.

In accordance with embodiments, the classification further includes class likelihoods per occupied seat.

In accordance with embodiments, the classification further comprises a smoothing process.

In various embodiments the method further comprising monitoring physiological data of at least one occupant of the vehicle. For example, the physiological data is selected from at least one of breathing rate, heart rate, heart rate variability and combinations thereof. Accordingly, the method may include assessing the occupant's mental condition based upon the physiological data.

In accordance with a second embodiment of the present invention there is provided a system for classifying one or more occupants in a vehicle cabin comprising one or more seats, the system comprising; at least one transmitter configured to transmit a plurality of Radio Frequency (RF) signals; at least one electromagnetic sensor connected to said at least transmitter, wherein said at least one electromagnetic sensor is configured to provide RF responses data of said substances; a Radio Frequency Signals Measurement Unit (RFSMU) configured to receive said RF responses and measure said RF responses; and a processor connected to said sensor said processor is configured to:

generate one or more 3D (three dimensional) images based on said RF responses;

process one or more consecutive 3D images of said obtained 3D images, said processing comprises:

remove background of said one or more consecutive 3D images; filter said one or more consecutive 3D images, said filtering comprises removing contribution of one or more of: sidelobes, multipath, thermal noise and cutter; cluster said filtered 3D images; associate one of the one or more seats to said one or more occupants and classify the one or more occupants based on feature computation said feature computation comprises: distribution of points for each cluster in said 3D images and according to said vehicle geometry.

There is provided according to the teaching of present invention, a multiple-input/multiple-output radar-based method using correlated movement to identity an object set, the method including: transmitting a plurality of transmitted radar signals towards a target object set, each signal of the plurality of signals emanating from a separate radar antenna; receiving reflected radar signals, each of the reflected radar signals having an amplitude attenuation and a phase shift relative to the transmitted radar signal; and decomposing the reflected radar signals into signal elements, each of the signal elements having a spatial component and a temporal component.

According to a further feature of the present invention, there is also provided
computing a periodicity of each of the signal elements from the temporal component associated with each of the signal elements.

According to a further feature of the present invention the periodicity is a breathing rate or a heart rate.

According to a further feature of the present invention, there is also provided computing a variance in the heart rate; and outputting the variance in the heart rate.

According to a further feature of the present invention the decomposing of the reflected radar signals is implemented through Blind Signal Separation, Independent Component Analysis, Principal Component Analysis, or Singular Value Decomposition.

There is also provided according to the teachings of the present invention a multiple-input/multiple-output radar-based method using correlated movement to identity an object set, the method including: transmitting a plurality of transmitted radar signals towards a target object set, each signal of the plurality of signals emanating from a separate radar antenna; receiving reflected radar signals, each of the reflected radar signals having an amplitude attenuation and a phase shift relative to the transmitted signal; assigning a voxel value to each voxel in accordance with a collective amplitude attenuation and a collective phase shift of the reflected radar signals; and decomposing the voxel values into voxel elements, each of the voxel elements having a spatial component and a temporal component.

According to the features of the current invention, there is also provided computing a periodicity of each of the voxel elements from the temporal component associated with each of the voxel elements.

According to the features of the current invention, the periodicity is a breathing rate or a heart rate.

According to the features of the current invention, there is also provided computing a variance in the heart rate; and outputting the variance in the heart rate.

According to the features of the current invention, the decomposing the voxel values is implemented through Blind Signal Separation or Independent Component Analysis.

According to the features of the current invention, the decomposing the voxel values is implemented through Independent Component Analysis.

According to the features of the current invention, the decomposing the voxel values is implemented through Principal Component Analysis.

According to the features of the current invention, the decomposing the voxel values is implemented through Singular Value Decomposition.

There is also provided according to the teachings of the present invention a multiple-input/multiple-output radar-based system for using correlated movement to identity an object set, the system including: a radar antenna array; at least one transmit/receive module configured to transmit radar signals and receive reflected radar signals through the antenna array; and a processor coupled to the array, the processor operative to: decompose the reflected radar signals into signal elements, each of the signal elements having a spatial component and a temporal component.

According to the features of the current invention, the processor is further configured to compute a periodicity of each of the signal elements from the temporal component associated with each of the signal elements.

According to the features of the current invention, the periodicity is a breathing rate or a heart rate.

According to the features of the current invention, the processor is further configured to compute a variance in the heart rate.

There is also provided according to the teachings of the present invention A multiple-input/multiple-output radar-based system for using correlated movement to identity an object set, the system including: a radar antenna array; at least one transmit/receive module configured to transmit radar signals and receive reflected radar signals through the antenna array; and a processor coupled to the array, the processor operative to: assigning a voxel value to each voxel in accordance with a collective amplitude attenuation and a collective phase shift of the reflected radar signals, decompose the voxel value into voxel elements, each of the voxel elements having a spatial component and a temporal component.

According to the features of the current invention, the processor is further configured to compute a periodicity of each of the voxel elements from the temporal component associated with each of the voxel elements.

According to the features of the current invention, the periodicity is a breathing rate or a heart rate.

According to the features of the current invention, the processor is further configured to compute a variance in the heart rate.

BRIEF DESCRIPTION OF THE DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the various selected embodiments may be put into practice. In the accompanying drawings:

FIG. 8a-8e depict image products at various stages of processing of passengers sitting in a car interior environment, in accordance with an embodiment of the invention.

Figure 1:
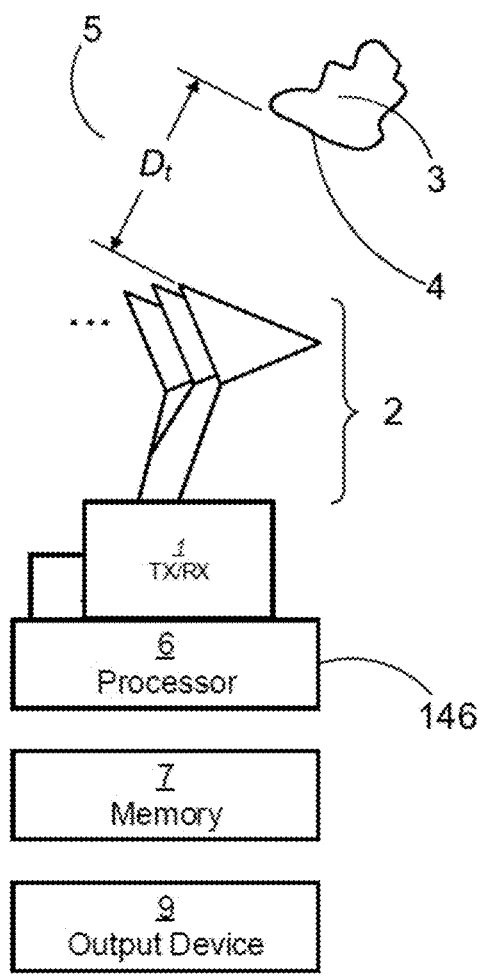
FIG. 1 is a schematic diagram of hardware employed in the MIMO detection system, in accordance with an embodiment of the invention.

It will be appreciated that for simplicity and clarity of illustration, elements shown in the figures are not necessarily drawn to scale and the dimensions of some elements may be exaggerated relative to other elements. In addition, reference numerals may be repeated among the figures to indicate corresponding or analogous elements.

DETAILED DESCRIPTION

In the following detailed description, numerous details are set forth to provide a thorough understanding of the invention. It will be understood by those skilled in the art that the present invention may be practiced without these specific details. In other instances, well-known methods, procedures, and components have not been described in detail so as not to obscure the present invention.

Embodiments of the present invention provide for RF signal processing to detect and obtain measurements from one or more elements of at least one target object. In related embodiments, detection and measurement is furthermore done without having to isolate or identify the specific part or parts which contribute to the correlated movement.

The term "complex target" herein denotes a target object having one or more parts not necessarily distinguished by their respective reflective properties alone (herein denoted as their respective "reflectivities"); but rather, through their correlated movement or motion.

Identification of target objects is based on their elements having dissimilar modes of motion. Similarly, identification of target object from a background is achieved from the contrast of their respective modes of motion.

Some applications provide for further classification of human targets into categories such as "adult", "infant", for example.

Other applications provide identifying regions or parts of the body. The human body is modeled as a collection of rigid bodies (the bones) connected by joints. Rigid bodies have the property that all points on the surface move in a correlated way, since they are all combinations of the 6 degrees of freedom of the rigid body. In these embodiments of the invention the grouping of correlated motions into elements facilitate the identification of regions or parts of the body.

Other applications provide detecting and measuring of physical activities, including but not limited to: walking, running, jumping; coordinated movement of the limbs; carrying objects; head turning; hand gestures; changes in posture; and the like.

Further applications of the present invention provide detecting correlated movement of individuals in specialized environments featuring particular background characteristics and monitoring requirements, including, but not limited to: vehicle interiors and other moving platforms; hospitals and other medical and care facilities; and public venues, non-limiting examples of which include airports and other transportation stations; shopping centers, warehouses, and other commercial establishments; residential and office complexes; museums, theaters, and entertainment halls; parks, playgrounds, and stadiums; and institutions such as schools.

Additional applications of the present invention include: medical and health-related applications; security applications; crowd management applications; and vehicle safety and comfort applications.

According to various embodiments of the present invention, a complex target can include the human body. In these embodiments, the parts of the body include, but are not limited to: the head, the neck, the individual limbs, and the torso. In certain embodiments, physiological activities such as respiration and heartbeat are detectable and measurable, without having to isolate or identify the region of the body responsible for respiration and heartbeat (i.e., the torso).

The term "correlated movement" herein includes movement of one physical element of an object set relative to another, volumetric changes of the elements themselves, changes in orientation, position, shape, contour, or any combination thereof.

The term "measure" and its variants herein denote not only determining quantitative values (including multivariate values), but also analyzing the values, particularly variations in time, and making qualitative characterizations thereof.

The term "voxel element" refers to an entity that has been decomposed from a series of 3D images, each of the images associated with its respective frame.

It should be appreciated that terminology is context dependent. In the context of the physical arena the same terminology is employed when referring to the signal or logical representation of the same entity.

A non-limiting example of such a qualitative characterization involves the measurement of multivariate physiological data, such as the heartbeat and respiration of a subject. Not only can these physiological activities be detected and measured as raw data, but it is also possible to include, as a measurement, a qualitative assessment of the subject's current physical and mental condition based on the breathing rate, heart rate, and heart rate variability. Mental condition is meant to include awareness level, sleepiness, fatigue, anxiety, stress and anger, among other conditions.

Turning now to the figures, FIG. 1 is a schematic block diagram of the MIMO imaging device including an antenna array 2 coupled to a radio frequency (RF) module 1 linked to a processor 6 in communication with memory 7 and output device 9, according to an embodiment. Output device 9 includes visual, audial devices, wireless devices, and printers.

As shown, the reflective elements of face 4 of target object set 3 provide differing reflectance as the radial distance Dt changes with time. Analysis of reflectance data in view of the reflectance data of previous time frames enables detection of correlated movement that advantageously provides discriminatory capability current unavailable in MIMO imaging systems. This is because traditional MIMO imaging systems repetitively construct images based on reflectance data of each time frame; independent of the reflectance data of the previous time frame. Accordingly, the use of correlated motion as differentiation tool constitutes an advance in the art of MIMO imaging.

Figure 2:
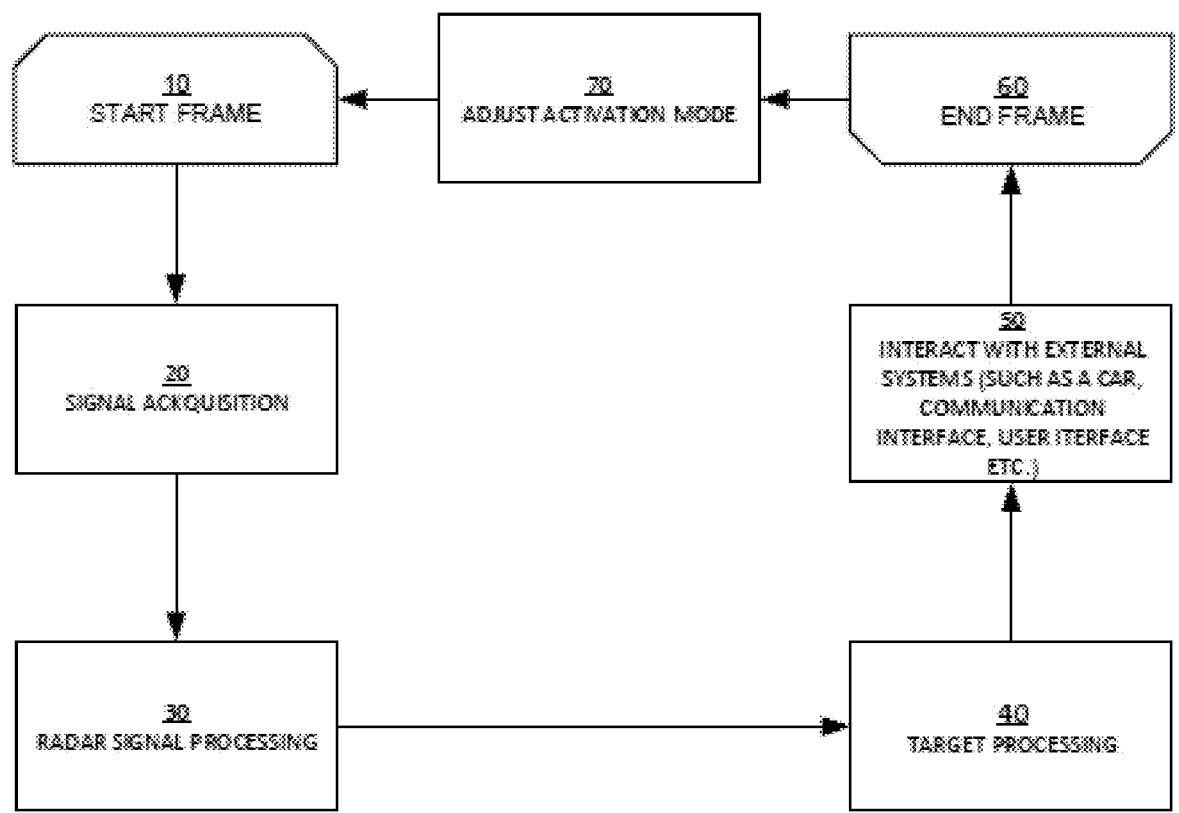
FIG. 2 is an overall flowchart illustrating the processing steps employed, in accordance with an embodiment of the invention.

FIG. 2 is a high-level flowchart illustrating a general processing scheme according to an embodiment of the present invention. The scheme can be described as a closed loop, where each iteration of the loop consists of a sequence of steps.

The loop begins at step 10, where the acquisition and processing of a new time frame is started. Frames are started at regular intervals of $\Delta t$ (meaning the frame rate equals $$\frac{1}{\Delta t}).$$

According to various embodiments of the invention, $\Delta t$ is selected so that target movement $\Delta D$ during $\Delta t$ is small compared to the wavelength of the radar signals $$\left(\text{i.e., } \Delta D \ll \frac{c}{4\pi f}\right)$$

to maintain continuity from one frame to another. For waves having a central frequency f, the wavelength is c/f, where c is the speed of light. When detecting and measuring periodic correlated movement of the target, imaging by a series of frames is a sampling process, so that the frame rate should be set according to the Nyquist criterion to avoid aliasing. Frames are indexed by t=0, 1, 2 . . . corresponding to time, where successive indices represent respective multiples of a $\Delta t$.

In step 20 radar signals are transmitted, received and processed to produce complex phasors, representing the amplitude and the phase of the each received signal relative to each transmitted signals. Step 20 is further elaborated in FIG. 3.

In step 30 several signal processing steps are performed, resulting in a set of components, each consisting of a spatial pattern and a trajectory (displacement vs. time). Step 30 is further elaborated in FIG. 4.

In step 40 components are used to identify targets, classify the targets and estimate target parameters of interest. Step 40 is further elaborated by FIG. 5.

In step 50 the identified targets and their estimated parameters are used to interact with external systems, including, but not limited to, vehicle systems (e.g. to activate a horn, turn on air conditioning, unlock a door etc.), communication interfaces (e.g. to alert a user using his mobile device) or user interfaces (to inform users and allow them to take action).

In step 60 frame processing is ended. In step 70 the system's activation mode is adjusted according to timers, identified targets and their parameters, as well as user inputs. The system activation mode controls parameters including, but not limited to, the number of frames per second the system captures (which determines $\Delta t$) and the transmitting power. In some cases, the system is put in standby mode for a period of time. Activation mode adjustment is done in order to conserve system power. The loop closes when the next frame begins (according to the timing dictated by the activation mode), and the system returns to step 10.

Figure 3:
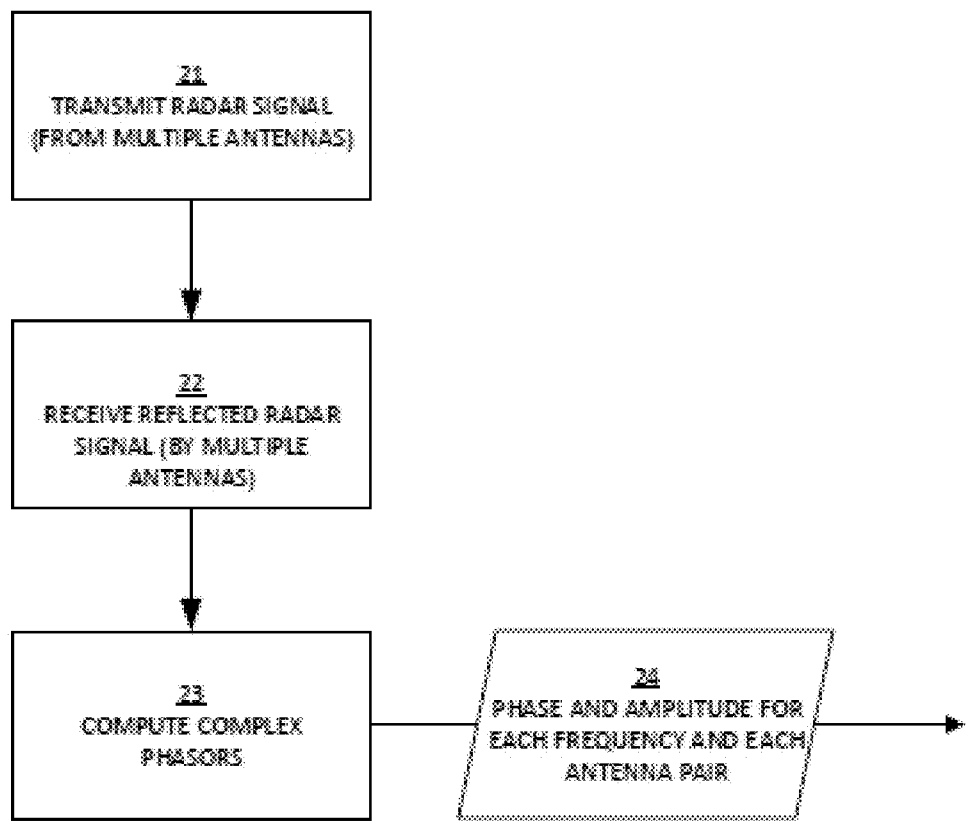
FIG. 3 is an overall flowchart illustrating general processing steps employed, in accordance with an embodiment of the invention.

FIG. 3 is a flowchart elaborating the RADAR SIGNAL ACQUISITION step from FIG. 2 (step 20). In Step 21, radar signals are transmitted from one or more antennas. If multiple antennas are used to transmit, the transmission can be done either sequentially (antenna-by-antenna) or simultaneously. In some embodiments of the invention antennas transmit simultaneously using a coding scheme such as BPSK, QPSK, or other coding schemes as is known in the art. Transmission may include a single frequency, or it may include multiple frequencies.

In step 22 the radar signals which have been reflected by targets in the physical environment surrounding the antennas are received by one or more antennas. Then in step 23 for each transmitted frequency and for each pair of transmitting and receiving antenna the received signals are processed to produce complex phasors, representing the phase and amplitude of the received signal relative to the transmitted signal (item 24).

Figure 4A:
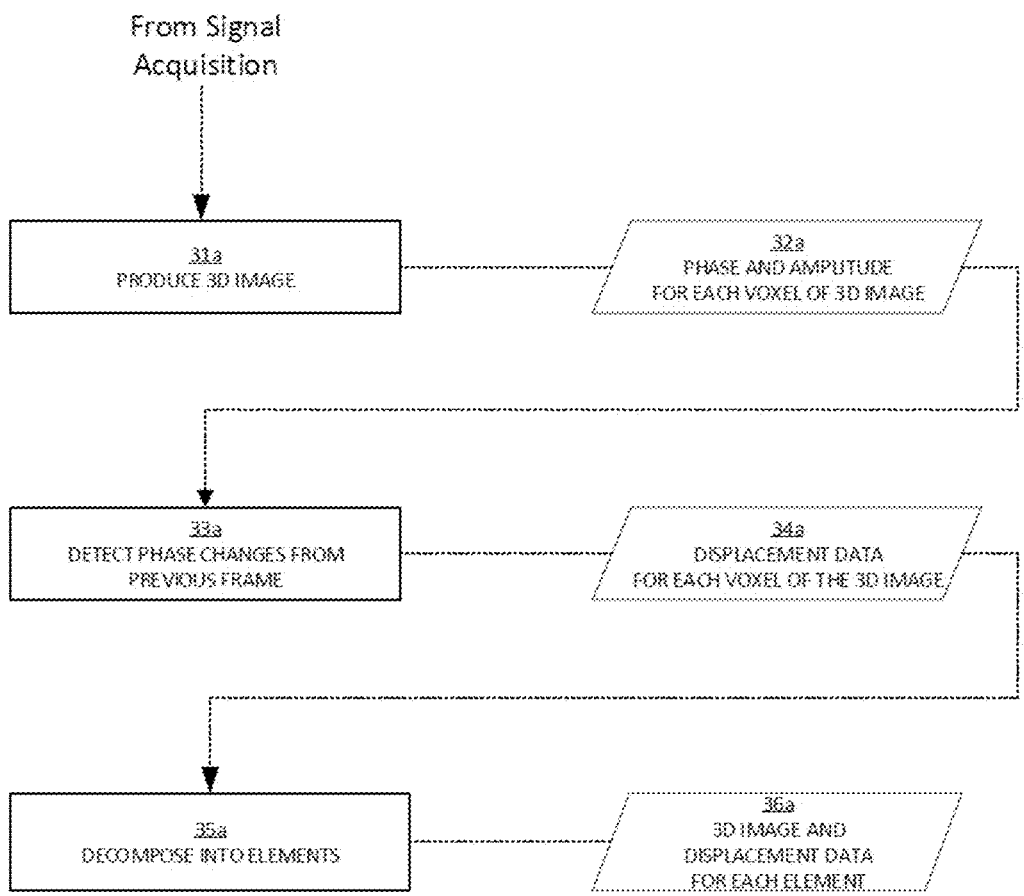
FIG. 4a is a flowchart illustrating the processing steps employed in a first embodiment of the radar signal processing stage, in accordance with an embodiment of the invention.

FIG. 4a is a flowchart elaborating the RADAR SIGNAL PROCESSING step from FIG. 2 (step 30) in an embodiment of the invention. In step 31a a 3D image is produced from the set of complex phasors describing the received signal. The image space representation is conceptually summarized as a data block 32a containing an image matrix $S=[S_{v,t}]$ with a voxel set V whose elements spatially conform to a system of coordinates. The particular system of coordinates for the voxel set can be chosen according to what is most convenient. Common choices include Cartesian coordinates ($v_{x,y,z}$) and polar coordinates ($v_{r,\theta,\varphi}$), but any other coordinate system is equally usable. Each voxel is associated with a single value $S_{v,t}=A_{v,t}e^{j\Phi_{v,t}}$ where $A_{v,t}$ is the amplitude and $\phi_{v,t}$ is the phase associated with a reflector at voxel v. The phase $\phi_{v,t}$ is determined by the radial displacement of the reflector in voxel v from the center of that voxel (designated $D_{v,t}$). The phase is related to the displacement by the following formula:

$$\phi_{v,t} = \frac{4\pi f}{c} D_{v,t}$$

where f refers to the central frequency. A single cycle extends over $\alpha$ radians, but an additional factor of 2 is needed because the reflection doubles the distance the waves travel.

In step 33a the value associated with each voxel at the current frame ($S_{v,t}$) is used together with the value associated with the same voxel at the previous frame ($S_{v,t-1}$), to obtain a robust estimate of the radial displacement between the two frames using the following formula:

$$\widetilde{\Delta D_{v,t}} = \frac{c}{4\pi f} \frac{\text{Im}[S_{v,t}S^*_{v,t-1}]}{|S_{v,t}||S_{v,t-1}| + \lambda\max_{V}(|S_{v,t}||S_{v,t-1}|) + \in} \quad (1)$$

where $\lambda$ and $\in$ are real scalar parameters that are selected to minimize the effects of noise on the final value. Typical values for $\lambda$ and $\in$ are small, with reasonable values being about 0.1 for $\lambda$ and about $1 \times 10^{-8}$ for $\in$.

According to another embodiment of the invention a slightly modified version of the formula is used, in order to provide better linearity of the estimated displacement:

$$\widetilde{\Delta D_{v,t}} = \frac{c}{4\pi f} \text{Arg}\left[\frac{[S_{v,t}S^*_{v,t-1}]}{|S_{v,t}||S_{v,t-1}| + \lambda\max_{V}(|S_{v,t}||S_{v,t-1}|) + \in}\right] \quad (2)$$

According to an embodiment of the invention, The estimated displacement data ($\widetilde{\Delta D_{v,t}}$) is recorded (item 34a) using a sliding window (which can be implemented, among other options by using a circular buffer), and in step 35a the radial trajectory component is decomposed into independent elements using Blind Signal Separation (BSS, also known as "Blind Source Separation"). In a related embodiment, the elements of the radial trajectory are separated by using Independent Component Analysis (ICA), a special case of BSS. In another embodiment, the elements of the radial trajectory are separated by Principal Component Analysis (PCA). In another embodiment, the elements of the radial trajectory are separated by Singular Value Decomposition (SVD).

In another embodiment of the invention, an online decomposition algorithm is used, avoiding the usage of a sliding window, allowing the separation of elements to be performed incrementally, frame-by-frame.

($\widetilde{\Delta D_{v,t}}$) is a matrix whose rows represent voxels, and whose columns represent frames. The decomposition algorithm extracts a factorization of ($\widetilde{\Delta D_{v,t}}$) in the form of factor triplets ("elements")

$$C_k = (u_{v,k}, \sigma_k, w_{k,t}) \quad (3)$$

where the matrix $[w_{k,t}]$ represents the aggregated frame-dependent (i.e., time-dependent) incremental radial displacements. And the matrix $[u_{v,k}]$ represents a spatial (voxel-dependent) pattern associated with the component.

The incremental radial displacements are summed to obtain an estimated radial displacement trajectory as a function of time:

$$\widetilde{D_{k,t}} = \sum_{t'=t_0}^{t}\left(w_{k,t'}\sigma_k \max_{V} u_{v,k}\right) \quad (4)$$

where the value is normalized to the largest observed incremental movement for the target. The term "summed" herein relates not only to a discrete representation in Equation (4), but also to "integration", according to a related embodiment which calculates the trajectory as an integral.

The spatial pattern $[u_{v,k}]$ and the radial displacement trajectory $\widetilde{D_{k,t}}$ are recorded as item 36a.

Figure 4B:
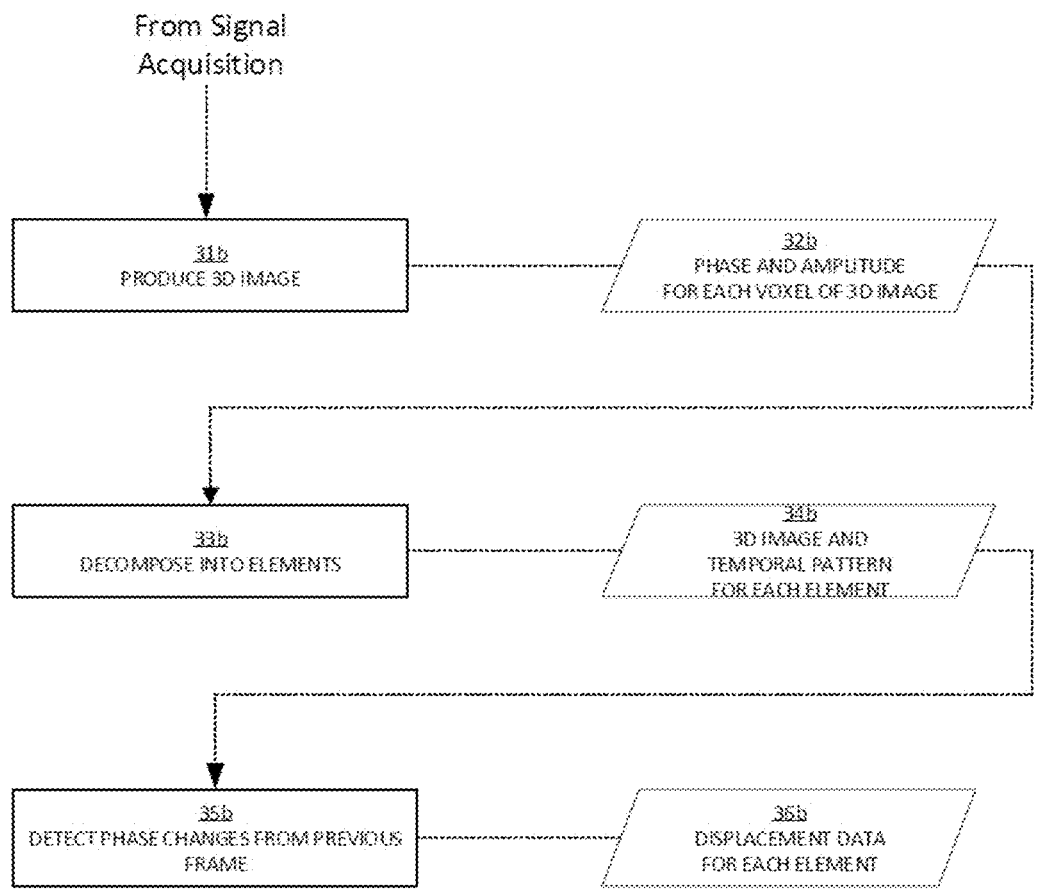
FIG. 4b is a flowchart illustrating the processing steps employed in a second embodiment of the radar signal processing stage, in accordance with an embodiment of the invention.

FIG. 4b is a flowchart elaborating the RADAR SIGNAL PROCESSING step from FIG. 2 (step 30) in an embodiment of the invention (separate from the embodiment described by FIG. 4a). In step 31b a 3D image is produced (item 32b), in a manner similar to the description hereinabove. In step 33b, the 3D image is decomposed using algorithms similar to the ones described hereinabove, producing a set of elements, each described by a 3D image and a temporal pattern consisting of complex phasors (item 34b). In step 35b each temporal pattern is processed using a phase detecting procedure similar to the one described hereinabove to produce displacement data for each element (item 36b).

Figure 4C:
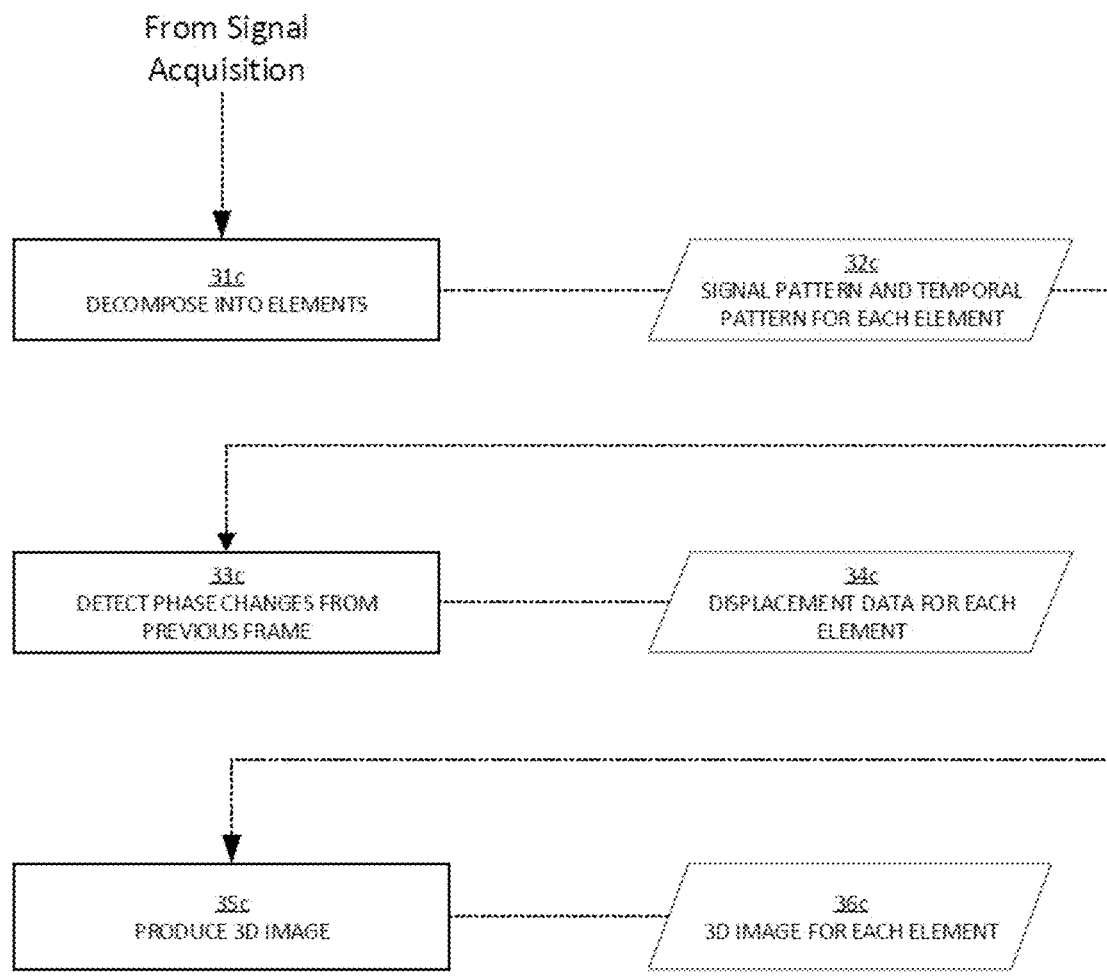
FIG. 4c is a flowchart illustrating the processing steps employed in a third embodiment of the radar signal processing stage, in accordance with an embodiment of the invention.

FIG. 4c is a flowchart elaborating the RADAR SIGNAL PROCESSING step from FIG. 2 (step 30) in an embodiment of the invention (separate from the embodiments described by FIG. 4a and FIG. 4b). In step 31c the complex radar signal is decomposed using algorithms similar to the ones described hereinabove, producing a set of elements, each described by a complex time-independent signal pattern and a temporal pattern consisting of complex phasors (item 32c). In step 33c, each temporal pattern is processed using a phase detecting procedure similar to the one described hereinabove to produce displacement data for each element (item 34c). In step 35c, each time-independent signal pattern is used to produce a 3D image for the corresponding element (item 36c), in a manner similar to the description hereinabove.

Figure 5:
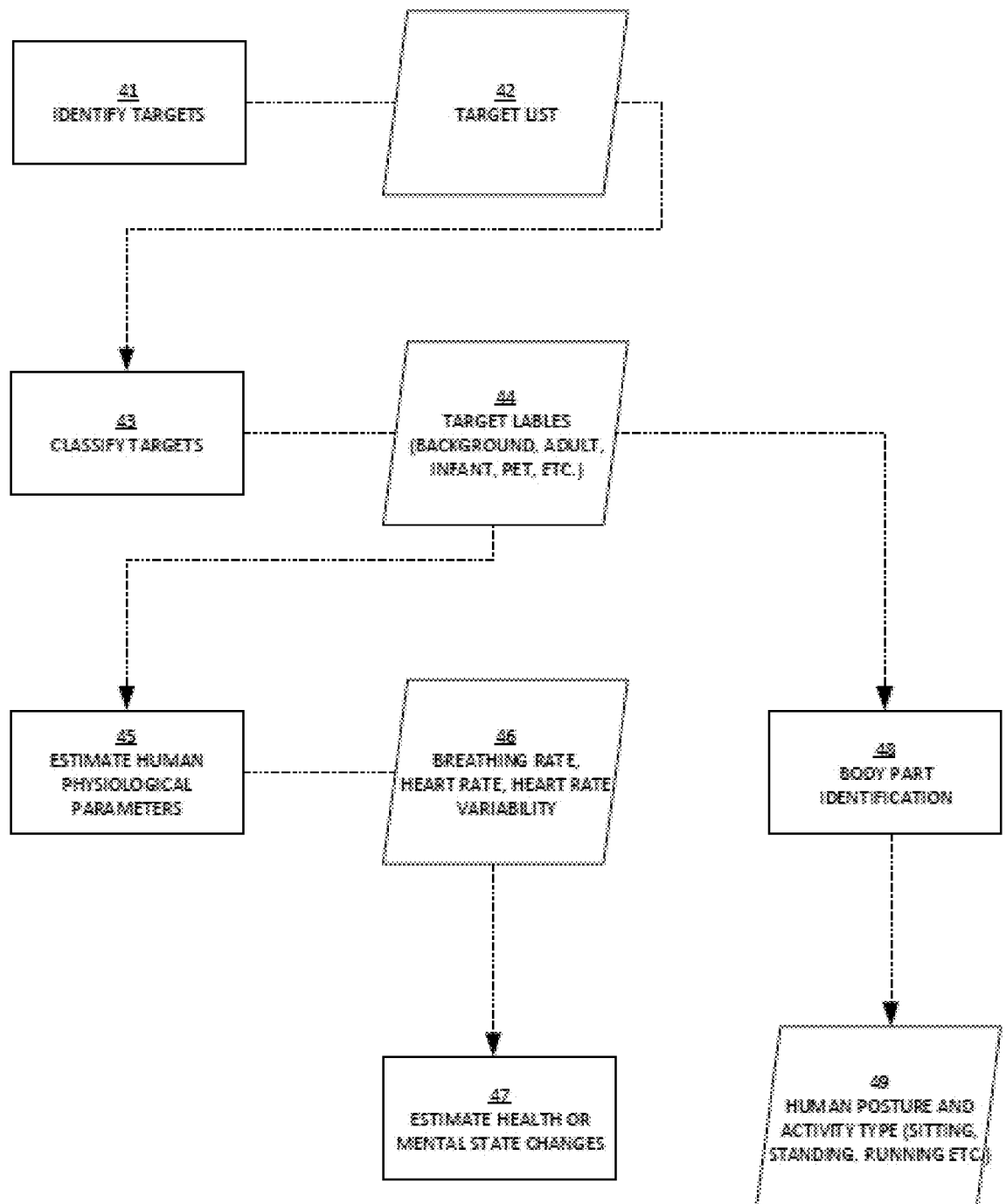
FIG. 5 is a flowchart illustrating the processing steps employed in the target processing stage, in accordance with an embodiment of the invention.

FIG. 5 is a flowchart elaborating the TARGET PROCESSING step from FIG. 2 (step 40) in an embodiment of the invention. In step 41, elements are grouped into targets, representing detected physical objects, by examining the spatial pattern of each element, producing a target list (item 42). In step 43 targets are classified, giving each target a label such as "background" (for example parts of a car interior), "adult", "infant", "pet" etc. (item 44). This classification is done by examining both the spatial pattern and the temporal displacement data for each element within the target.

In step 45, the temporal displacement data of the elements within each human target are used to produce a spectral power distribution model, describing periodicities in the target's movement. In an embodiment of the invention, Welch's method is used to produce the spectral power density model (a non-parametric spectral model). In another embodiment, an (Auto Regressive Moving Average) ARMA model (a parametric spectral model) is used to produce the spectral power density model. Physiological parameters are estimated for human targets, including the breathing rate, heart rate and heart rate variability. Breathing rate and heart rate are estimated from the location of peaks in the spectral power distribution. In an embodiment, using Welch's method, heart rate variability is estimated from the width of the spectral peak corresponding to the heartrate. In another embodiment, using an ARMA model, the heart rate variability is estimated from the parametric representation of the ARMA model itself.

In step 47, the breathing rate, heart rate and heart rate variability are monitored for changes, indicating health or mental state changes.

In step 48, the 3D image associated with each element of a human target is used to identify the element with one or more human body parts. This identification is then used to generate additional data such as human posture and activity type (sitting, standing, running, etc.), as described hereinabove.

Figure 6:
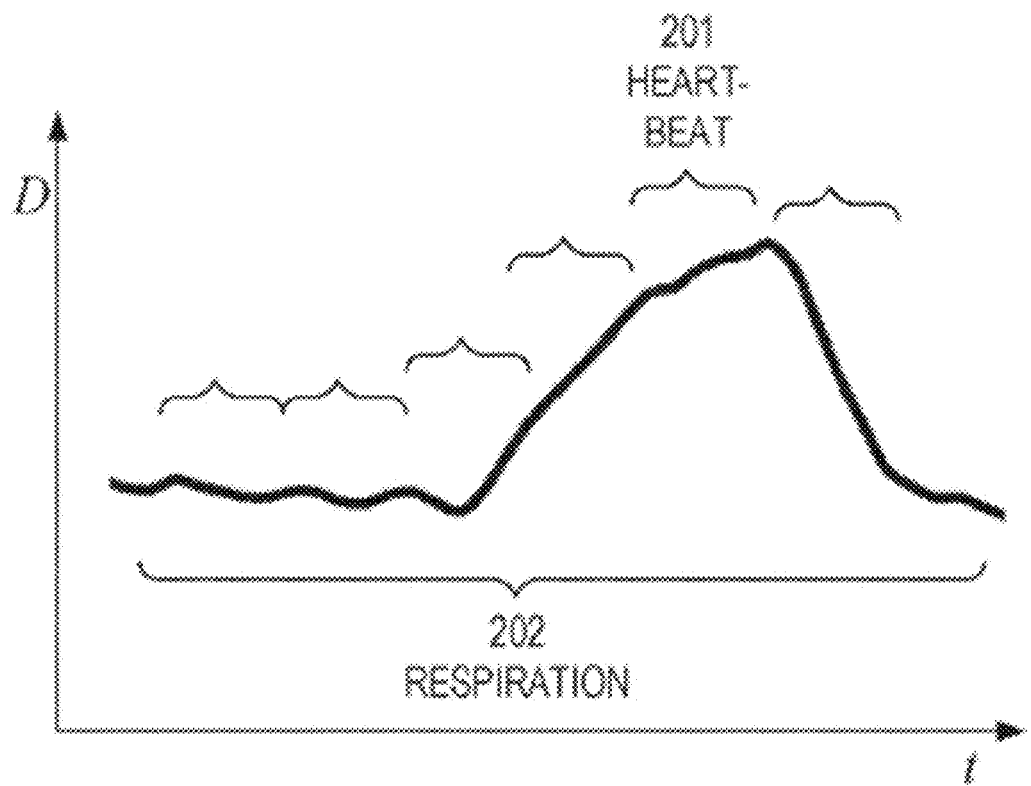
FIG. 6 is a plot of radial displacement as a function of time, as measured for a human subject, in accordance with an embodiment of the invention.

FIG. 6 shows a graph of radial displacement versus time, as measured for a human subject by a method and apparatus according to an embodiment of the present invention. A portion 201 shows a detected heartbeat, and a portion 202 shows a detected respiration. It is noted that according to this embodiment of the invention, it is not necessary to isolate the individual region of the body responsible for heartbeat and respiration.

Figure 7:
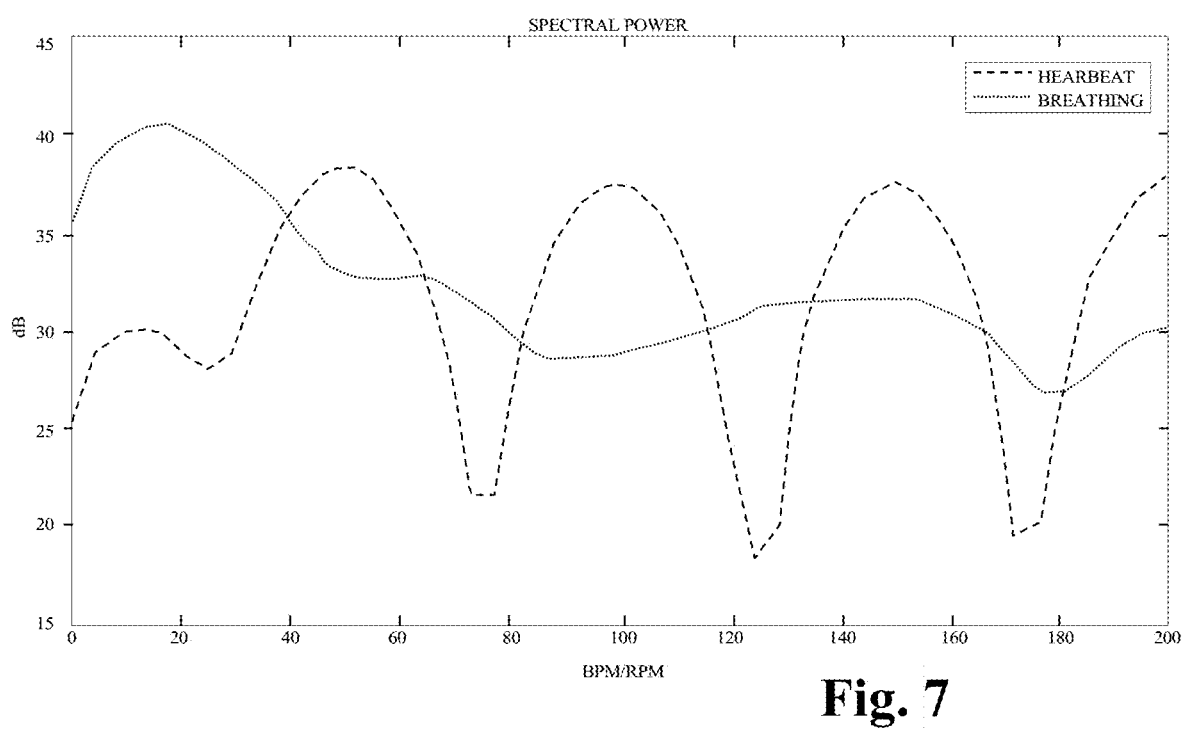
FIG. 7 depicts two plots of spectral power density for two identified elements, in accordance with an embodiment of the invention.

FIG. 7 depicts a plot of the spectral power density of two elements identified by a method and apparatus according to an embodiment of the present invention.

In this embodiment, the sensor has been positioned close to a human subject, the two elements represent two modes of motion, one originating from the respiratory motion of the human subject, and the other originating from the heartbeat motion of the human subject. As can be seen, the elements represent motions which have different periodicity from one another. Each element is then used to calculate the corresponding rate parameter: breathing rate (measured in RPM—respirations per minute), and heart rate (measured in BPM—beats per minute).

FIGS. 8a, 8b, 8c, 8d, and 8e depict image products at various stages of processing of passengers sitting in a car environment.

By way of introduction, a car interior environment has several factors that contribute to the difficulty of identifying and separating passengers from one another and from the car interior background when imaging; passenger proximity, difference in passenger reflectivity, and car vibration.

Passenger proximity refers to passengers sitting next to each other and even contact each other, as is common in the back seat. Accordingly, these backseat passengers can appear as a single target object, when considering reflectance data of each frame separately.

The difference in passenger reflectivity can be very high due to difference in size (e.g. adult vs infant), positioning, and orientation. Differences in passenger reflectivity may degrade detection performance (false positive and false negative rate).

Car vibration also presents a significant challenge for current state of the art MIMO imaging techniques. The difficulty in detecting a change in position is exacerbated as passenger background (the car interior itself) vibrates and alters its reflective properties. As noted above, these imaging obstacles are resolved through the use of correlated motion as the differentiating parameter.

FIG. 8a depicts a 2D top view projection of a 3D image, generated by a MIMO radar installed in the roof of the passenger cabin of the car. The image represents a single captured frame. A white rectangle has been added to indicate the boundary of the car interior. The specific scenario being shown is that of an adult sitting in the driver seat (top left corner of the white rectangle), an infant sitting in the passenger front seat (top right corner of the white rectangle), and another adult sitting in the right seat in the back row (bottom right corner of the white rectangle). As can be seen, it is extremely difficult to identify the infant, due to its low reflectivity compared to the adult passengers. Objects associated with adult passengers mask the signal reflection from the infant.

FIG. 8b, 8c, 8d, show the spatial pattern associated with three elements which have been decomposed from a sequence of frames, by identifying the correlated motion of each individual passenger. These spatial patterns allow for an easy identification of three passengers.

Figure 8E:
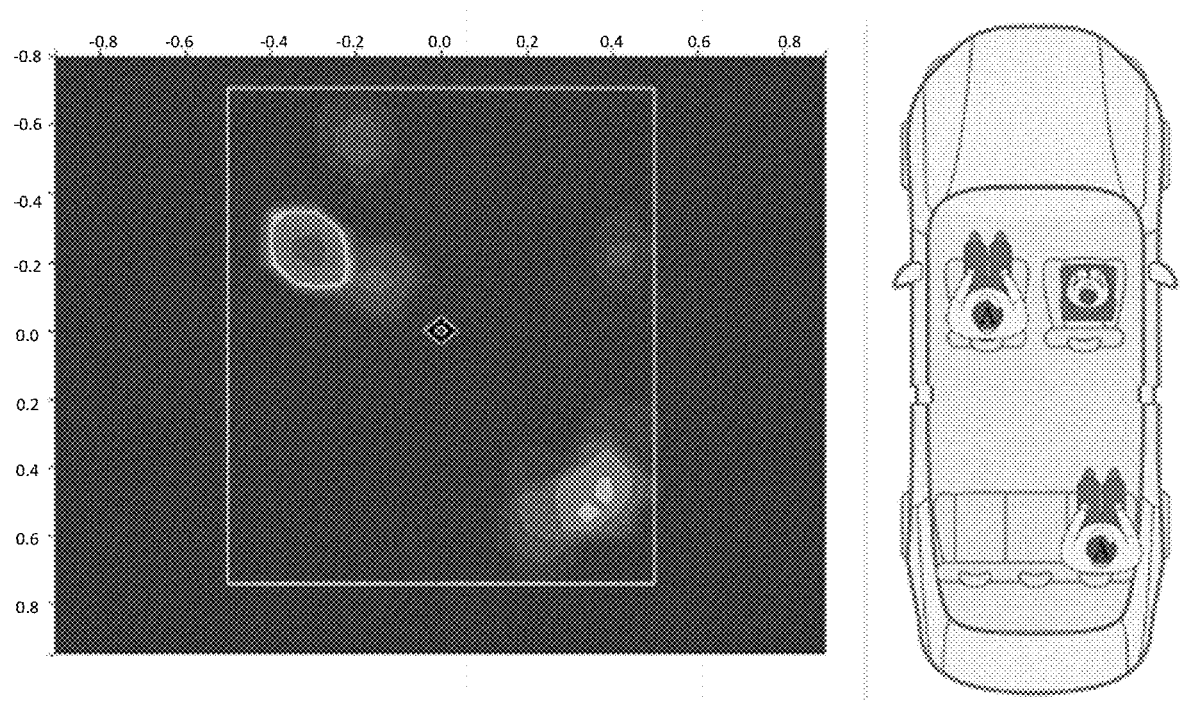

FIG. 8e shows a screenshot of a user interface, used as an output of the system. On the left side is an image produced by filtering and then recombining the spatial patterns shown in FIG. 8b, 8c, 8d. On the right side is a graphical summarization of the occupancy state reported by the system, correctly identifying the two adults and the infant in the correct positions. The classification of passengers into adults and infants is done by examining the spatial pattern for each detected element.

The separated components characterize the spatial movement modes associated with each type of movement, e.g. the spatial movement mode associated with respiration and the spatial movement mode associated with heartbeat.

The sets of voxels over which the movement is characterized can originate from a target tracking function, or it can originate form a priori knowledge, such as the candidate seating locations of persons in a car. The set of voxels may encompass multiple people, where the set of movement modes would encompass, for example, the respiration patterns of those multiple people. In the case of a moving vehicle, the spatial movement modes may include motion induced by the vibration of the vehicle, and the measured voxels may include reference objects such as empty seats. In other examples the measurement may include moving objects in the environment, such as ceiling fans, so as to separate fluctuations induced by such objects and movements induced by people of interest.

According to some embodiments, the system is be configurable to operate in various detection or activation modes; high detection mode, a medium modes, or a standby mode in which the fps and respective time durations are set by a user or manufacturer. Following are examples of activation modes:

High active mode: Capture rate of 30 frames per second (fps) for a period of 12 seconds, then a capture recess for 18 seconds, and repeating these two steps 6 sequential times (overall 3 minutes);

Medium active mode: capture rate of 10 fps for a period of 9 seconds, then a capture recess for 51 seconds, and repeating these two steps 10 sequential times (overall 10 minutes);

Standby mode: No capture for a period of 10 minutes, while former data captured and processed is saved for future analysis and comparison.

The system provides further flexibility by providing a configuration provision to activate in various activation modes, each for a predefined time or for a predetermined number of cycles or be activated by a combination of predefined time period and cycles.

Furthermore, according to some embodiments, the system can automatically change from one activation mode to another, responsively to collected data.

According to some embodiments, the system can be activated (turned "ON") manually, and according to some embodiments, the system can be automatically activated responsive to predetermined instructions (for example during specific hours) and/or a predetermined condition of another system.

Additional power saving provisions include provisions to activate a reduced number of radar, transmit/receive modules, and processors in accordance with different power consumption or activation modes.

According to some embodiments, the system can be temporarily triggered OFF or temporarily activated in a "standby" mode, for power resources conservation.

Figure 9:
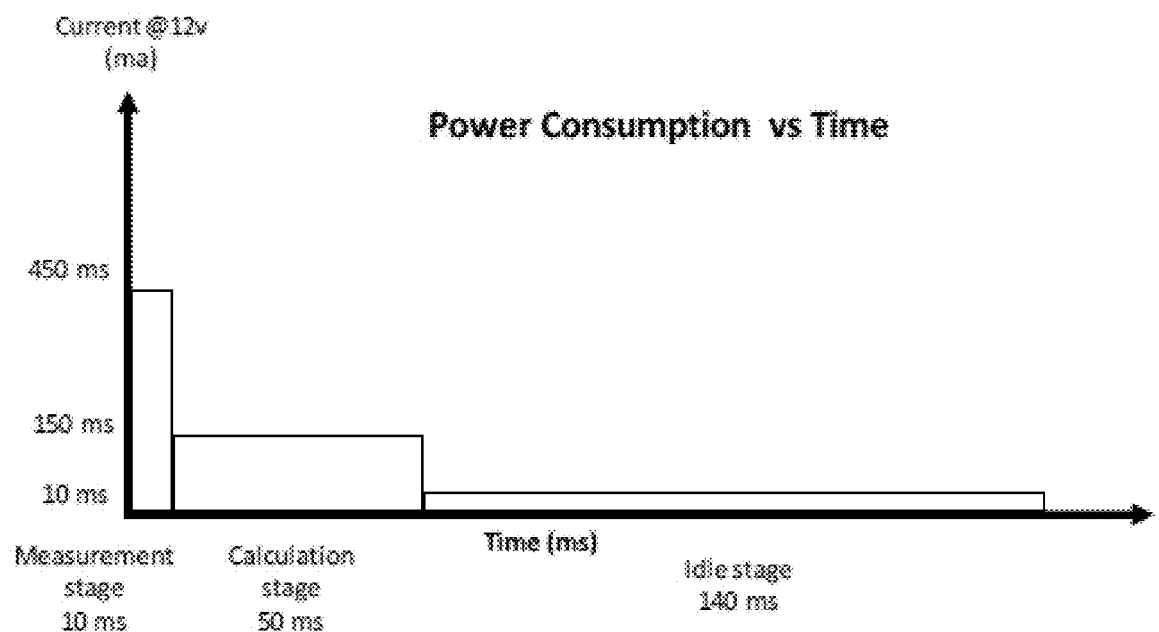
FIG. 9 is a graph depicting operating stages of one operating cycle employed during active detection modes, in accordance with an embodiment of the invention.

FIG. 9 depicts operating stages of one operating cycle employed during active detection modes, in accordance with a certain embodiment. As shown, the operating cycle includes a measurement stage, calculation stage, and an idle stage.

In the measurement stage, capture of a complex target object employs a current of 450 mA via a voltage of 12v, for a time slot of 10 msec, at a full frame rate, for example between 15 to 25 frames per second (fps).

During the calculations stage, where calculations are executed in accordance with at least some of the above-mentioned methods to identify a motion, using a current of 150 mA via a voltage of 12v, for a time slot of 50 msec;

During the idle stage, a current of 30 mA via a voltage of 12v is employed, for a time slot of 140 msec to ensure memory retention previously captured or calculated data.

According to some embodiments, the methods and system mentioned above, can be implemented for various of monitoring and alerting uses. In a certain application, for example, a baby/toddler sitting in the back seat of a vehicle or in a crib is monitored. The device is configured to activate an alarm responsively to detection of a threshold variation change in breathing rate or heartbeat rate.

Another vehicular monitoring application is the field of detection of a baby or a toddler remaining in the vehicle after a threshold amount of time following engine disengagement and door locking.

In a certain embodiment the monitoring device is implemented within a vehicle to monitor occupants.

In a certain embodiment, the vehicular monitoring device is configured to be activated when the engine is OFF and/or the doors are locked in accordance with at least one of the above mentioned high and medium activation modes for a predetermined number of cycles and/or time period. The device is linked to the engine and locking system so at to provide such actuation functionality. Situations in which no motion is observed the monitoring device assumes a standby mode for a configurable time period.

According to some embodiments, the alert is selected from either activating the vehicle's horn, activating the vehicle's air ventilation, opening the vehicles windows, unlocking the vehicle, sending an alert to an application user, sending an alert to emergency services, and any combination thereof. According to some embodiments, alert is repeated until the system is manually switched OFF.

The monitoring device is configured to sequentially repeat the "monitoring" and "standby" operating modes, until: the vehicle is switched "ON", wherein the system is either manually turned OFF, automatically turned off, or continues to monitor in accordance with either the passage of a threshold period of time or an achievement of a threshold number of repetitions.

Similarly, the device can be employed to the monitor the elderly or sick at one's bed and activate an alarm responsively to a threshold variation in breathing rate, heart rate, or heart rate variability.

The device-linked alarm includes audial alarms, visual alarms, or the combination of both, and in certain embodiments the alarm is activated remotely through any of a variety of wireless technologies.

It should be appreciated that embodiments formed from combinations of features set forth in separate embodiments are also within the scope of the present invention. Furthermore, while certain features of the invention have been illustrated and described herein, modifications, substitutions, and equivalents are included within the scope of the invention.

Aspects of the present disclosure relate to systems and methods for classifying vehicle occupants in the various seats of the vehicle.

Systems and methods intended for such tasks are required to be able to operate around the clock, including in the dark, and to detect and classify occupants even if concealed, such as covered by a blanket for example. Reliable classifications should be provided regardless of the car state, immaterial of whether the ignition is on, the air-conditioning is working, whether the vehicle is stationary or moving, and even if moving on a bumpy road.

Classification of occupants may include various categories such as, but not exclusively, age group, weight, size, indication whether a child seat exists, position of the occupant, animal vs. human, child vs. adult, male vs female as well as objects like water bottles and hanging shirts (which tend to move while driving) and the like.

Although classifying the occupants is important, it is also frequently required to simultaneously respect their privacy, and to avoid detecting and recording identifying details.

Possible technologies for classification occupants may include pressure sensors under the seats, a camera which may be assisted by a depth camera of any kind, a stand-alone depth camera, ultrasonic imaging and radar imaging.

The main drawback of cameras is the required external light source, and the inability to penetrate through non-transparent materials. Additionally, the image resolution of cameras may invade privacy.

Depth cameras which emit their own light in infrared frequencies for example, are capable of operating in darkness, but may be saturated during daytime. Additionally, they often do not penetrate through seats and blankets.

Pressure sensors provide information about weight, but do not provide any information about shape or size of the occupant, and therefore, they are generally insufficient.

On the other hand, radar and ultrasonic imaging systems can be implemented using waves with a wavelength in the order of 1 cm. Such systems are capable of operating in darkness and can penetrate objects which are not transparent to visible light. The wavelength of 1 cm is sufficient for classification of the occupants into groups such as, age group, weight, size, indication whether a child seat exists, position of the occupant, etc. . . . as outlined above to accord with technical and legal requirements and safety rules, but is insufficient to identify them. Radar and Ultrasonic sensors can be used to identify passengers under a blanket, and are not saturated by natural sources of light and sound.

Figure 10:
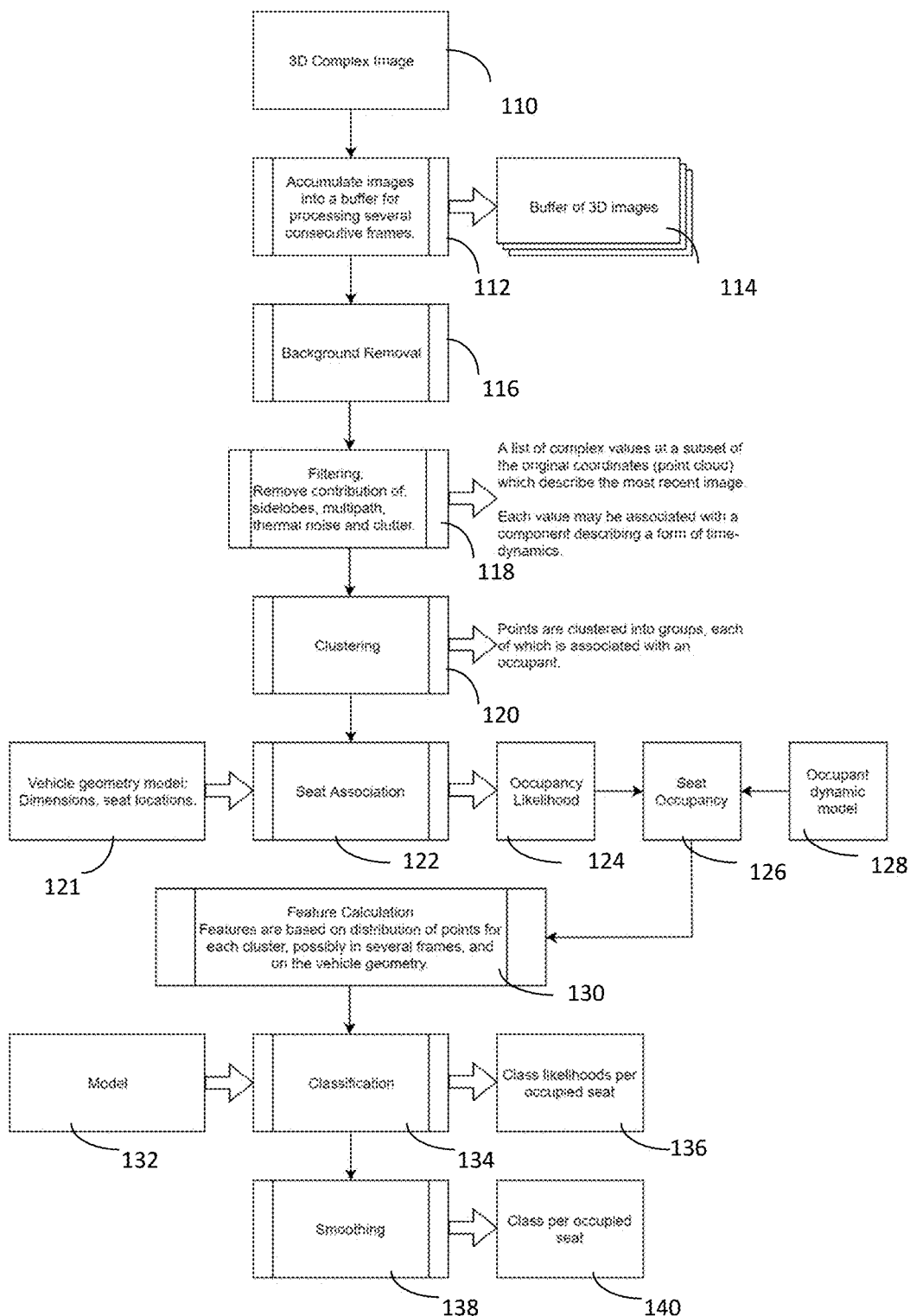
FIG. 10 is a flow diagram of showing how a 3 dimensional complex radar image of the cabin of a vehicle may be used to extract data regarding which seats are occupied and for classifying the occupant of each occupied seat.

With reference to FIG. 10, a method is described for converting a 3D complex image obtained inside a vehicle over a grid of coordinates into a list of occupants of the vehicle with an associated class.

The method comprises obtaining a 3D complex image of the occupants of a vehicle cabin—step 110.

Image accumulation is required for obtaining a dynamic model of the occupants. The three dimensional image (complex values at a predefined set of coordinates) is stored as a row vector in a matrix. The matrix may store a predefined number of images (frames), or the number of frames to be stored may be variable.

An array of transmitting and receiving elements is used in order to generate a set of complex values associated with coordinates in a predefined area or volume inside and possibly around a vehicle. These values and associated coordinates are referred to as a complex 3D image. The magnitude of a complex value may indicate the probability that a reflecting object is located in that coordinate.

US Patent Publication 2019/0254544 titled DETECTING AND MEASURING CORRELATED MOVEMENT BY ULTRA-WIDEBAND MIMO RADAR incorporated herein by reference provides an exemplary method for obtaining a 3D complex-image of moving occupants is described. Another method is described in J. M. Lopez-Sanchez, J. Fortuny-Guasch, "3-D Radar Imaging Using Range Migration Techniques", IEEE transactions on antennas and propagation, vol. 48, no. 5, May 2000, pp 728-737, which is incorporated by reference herein.

As a particular case, the image may store real values only, representing, for example the magnitude in each voxel.

A known algorithm for constructing such a complex image for an array of transmitting and receiving elements is the Delay and Sum algorithm (DAS). A variation on the DAS algorithm can be found in Giulia Matrone, Allesandro Stuart, Giosue Caliano, Giuvanni Magenes, "The Delay Multiply and Sum Algorithm in Ultrasound B-Mode Medical Imaging", IEEE Transactions on Medical Imaging, Vol. 34, number 4, April 2015 which is incorporated herein by reference. More complex algorithms include algorithms for solving inverse problems. A review of solving inverse problems in imaging can be found in Alice Lucas, Michael Iliadis, Rafael Molina, Aggelos K. Katsaggelos, "Using Deep Neural Networks for Inverse Problems in Imaging: Beyond Analytical Methods", IEEE Signal Processing Magazine, Volume 35, Issue 1, January 2018, pp. 20-36, as well as in Michael T. McCann, Kyong Hwan Jin, Michael Unser, "Convolutional Neural Networks for Inverse Problems in Imaging: A Review", IEEE Signal Processing Magazine, Volume 34, Issue 6, November 2017, pp. 85-95 both of which are also included by reference.

When classifying occupants, it may be assumed that they will show at least slight movement over time, such as chest movements and breathing, so phase variations over time for a given coordinate may indicate movement of the object. This can be detected when reviewing multiple frames. Images may be accumulated (step 112) in a buffer 114.

The walls of the cabin, seats and other constant and stationary features may be subtracted from the detected signals by a background removal algorithm—step 116.

Background removal may be achieved by as subtraction of the mean value for each coordinate, for example, in one or both of the following ways:

Applying a high-pass filter on each of the coordinates

For each column in the matrix of images, subtracting the mean value of the column.

Filtering—step 118 is performed to remove the contribution of sidelobes, multipath, thermal noise and clutter. The filtering step of FIG. 10 is performed based on dynamic behavior is expanded on in FIG. 11.

The points are then clustered into groups, each of which is associated with an occupant (step 120).

Data corresponding to the vehicle geometry model, dimensions and seat locations is provided—step 121. Each cluster is associated with a seat—step 122, and an occupation likelihood statistic is generated—step 124, such that a threshold value is used to decide whether or not a seat is occupied—step 126. This decision may be supplemented by results of an occupant dynamic model—step 128.

Features of each cluster are calculated, based on the vehicle geometry and the distribution of points for each cluster, possibly over several frames—step 130.

A model 132 is applied to the features classification of step 130 to create a classification 134 which assesses the likelihood that an occupied seat is assigned to a specific class, and this can be smoothed—step 138 to allocate the occupier of a seat to a specific class.

Occupation determination and classification procedure may involve various methods particularly machine learning. For example, a neural network may be trained to determine occupation or perform classification into required category groups, although other classification methods may be used. Parameters of the function may be optimized using a learning algorithm. Where the function is implemented in the form of a neural network, a feed forward neural network may be utilized where appropriate. Additionally or alternatively, a network with feedback may be used to take account of historical features such as an RNN (recurrent neural network), an LSTM (Long and Short Term Memory) network, or the like.

Alternatively, or additionally values for the coordinates of every box around a seat may be used as an input to a network, rather than a list of particular features. Accordingly, a convolutional neural network (CNN) may be appropriate. It will be appreciated that combinations of any of the above, such as a combined CNN with an RNN may be preferred. The values of coordinates within each box may be used for determining whether the seat associated with a particular box is occupied.

Although neural networks are described above for illustrative purposes, other classification algorithms may be additionally or alternatively used to provide the required classification, for example SVM (support vector machine), decision trees, an ensemble of decision trees, also known as decision forest. Other classification algorithms will occur to those skilled in the art.

Figure 11:
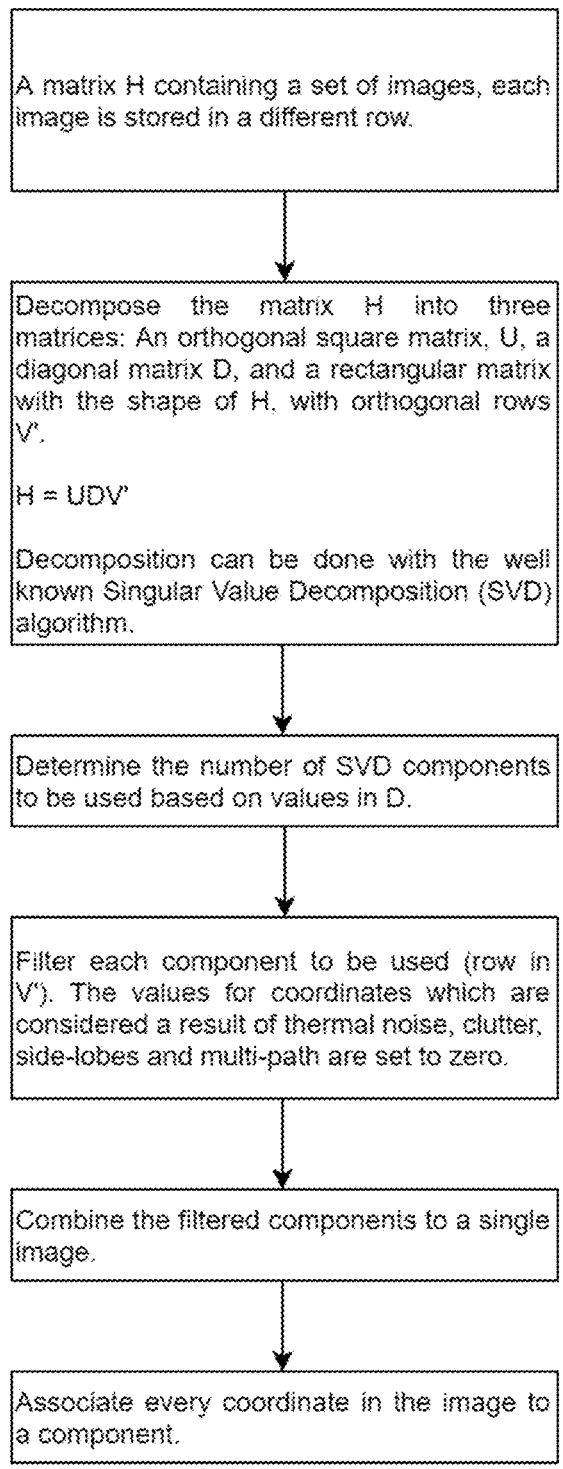
FIG. 11 is a flow chart of the Filtering step.
Figure 12:
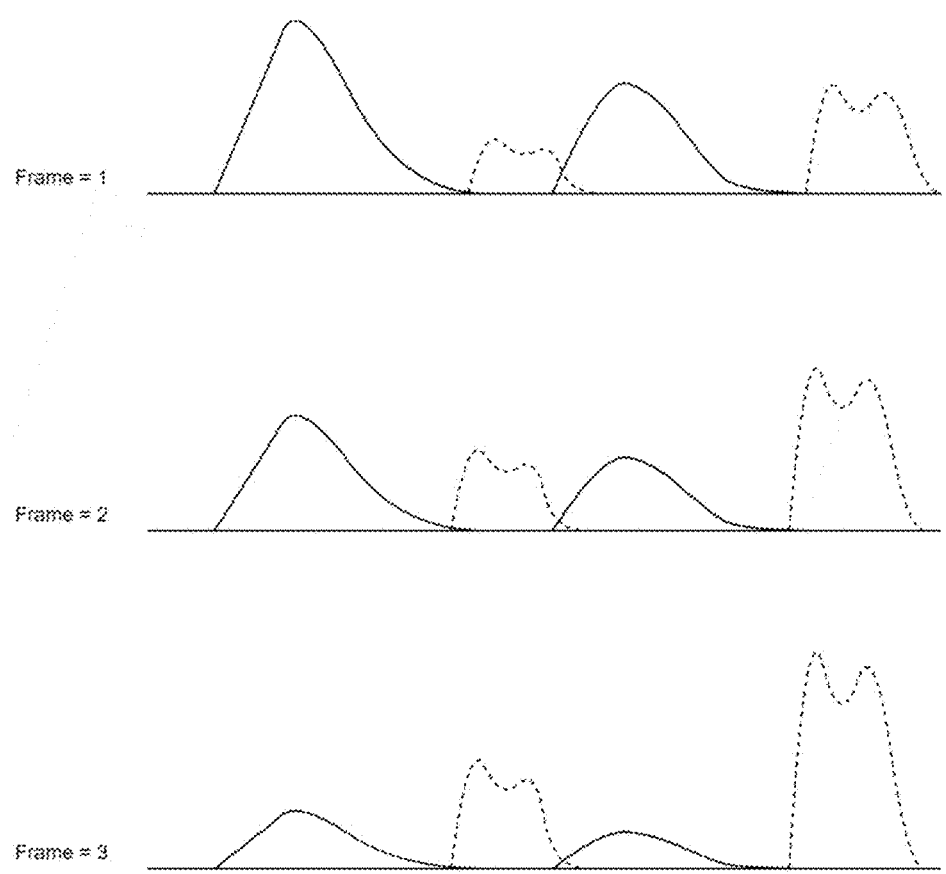
FIG. 12 is a schematic illustration of the filtering step.
Figure 13:
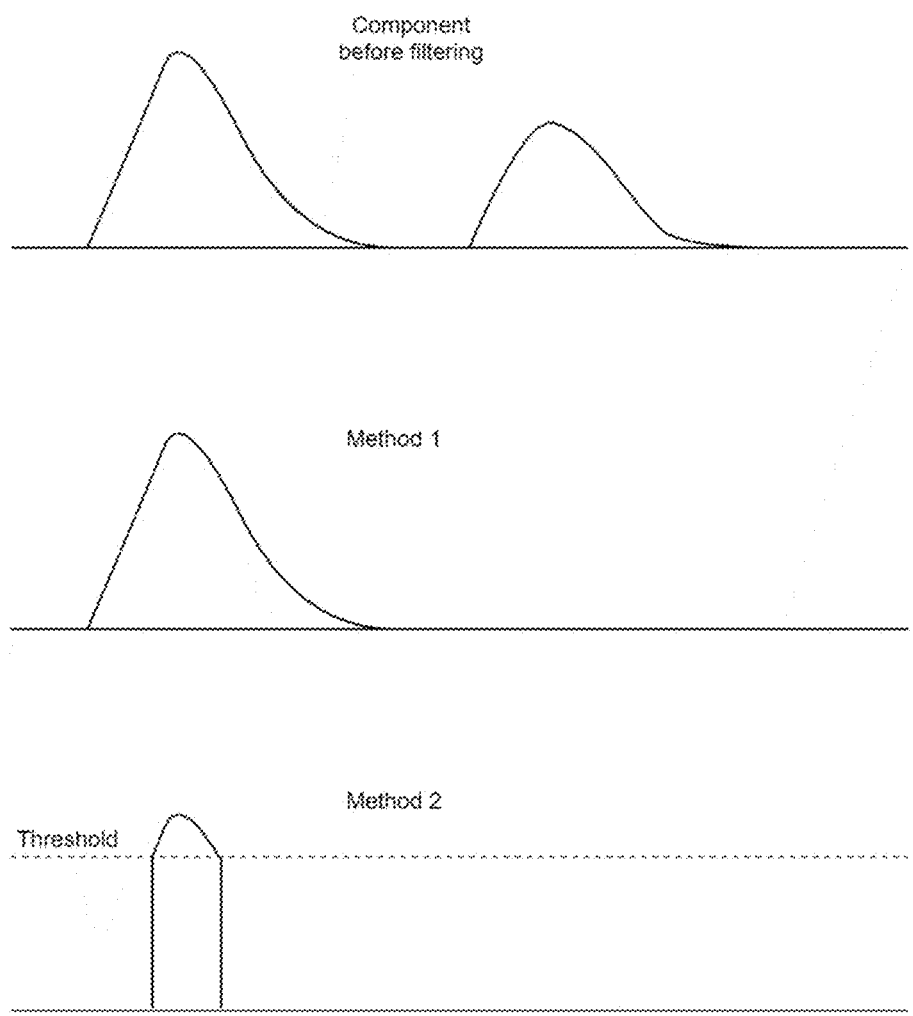
FIG. 13 is a schematic illustration of the filtering step.

FIG. 11-13 show the method of filtering using dynamic behavior.

Decomposition (SVD)

Multipath, grating-lobes and side-lobes, have a similar dynamic behavior. Therefore singular value decomposition (SVD) tends to represent them using a single vector with a time varying coefficient.

With reference to FIG. 12, the time-evolution of a signal representing an image is shown. The set of images can be decomposed into two components, one of which is drawn with a solid line and the other with a dashed line. The magnitude of one component (solid line) decreases with time and the other increases with time. SVD decomposition can provide these components.

The mathematical formulation is as follows: Matrix H stores a set of images. Each row represents an image. the matrix H may be decomposed, for example, using a standard algorithm called singular value decomposition. The matrix is decomposed into three matrices.

$$H = U \cdot D \cdot V^H$$

In the decomposition, U represents a rotation matrix, D is a diagonal matrix (not necessarily square), and $V^H$ is a matrix with equal dimensions to H with orthogonal rows. Rows of $V^H$ contain components such as shown in the figure above.

Determining the Number of Components

Determining the number of Required Components can be done with criteria based on distribution of the singular values, the values on the main diagonal of matrix D. One way is to select components which correspond to the largest singular values which add up to a percentage of the total value, for example 95%.

A different method is based on searching for a corner point in a graph of ordered singular values.

Both methods are known in the art.

Alternative Decompositions

While SVD can be used for decomposition, this should be regarded as an example only for a broader class of decomposition options.

Alternative decompositions include, for example the following:

Independent Component Analysis (ICA)

This decomposition assumes that the observations are a linear mixture of statistically independent sources. The goal of the decomposition is to search for the independent sources.

It is formulated as follows:

$$\begin{pmatrix} \text{observations} \\ n_{observations} \times n_{dimensions} \end{pmatrix} = M \cdot \begin{pmatrix} \text{sources} \\ n_{sources} \times n_{dimensions} \end{pmatrix}$$

Where is an unknown mixing matrix. The ICA provides the sources which can be treated as components associated with occupants.

The inventors have noticed that at high SNR levels, performance of ICA often exceeds that of SVD in separating different occupants to different components or sources.

Component Filtering

Filtering each component is based on the assumption that a component, which describes a form of time-domain movement, should have localized energy. The filtering operation should preferably maintain localized values. In the following two filtering methods are described.

Method 1: Divide the image into high energy blobs and maintain only the blob with the highest energy.

Method 2: Maintain only coordinates with energy above a threshold. The threshold can be either relative to a peak value or absolute.

The two methods are depicted in FIG. 13 which demonstrates that the filtering operation zeros many of the coordinates. Generally, a mask can be defined, that decreases unwanted values instead of zeroing them.

Combining Filtered Components to a Filtered Image

Combining the filtered components into an image can be done on a component by component basis.

The following notation is used herein for describing the method.

$\tilde{D}_n = D$ where all elements except for (n,n) are set to 0.
$\tilde{V}^H$ = Filtered components of $V^H$
$\tilde{V}_n^H = n^{th}$ row of $\tilde{V}^H$
$\tilde{H}_k^{(n)} = k^{th}$ row of $\tilde{H}^{(n)} = U \cdot \tilde{D}_n \cdot \tilde{V}^H$ One or more of several different methods may be used to generate a final image, as described below.

A first method involves averaging of the absolute value of several rows of $\tilde{H}^{(n)}$:

$$image^{(n)} = \frac{1}{C} \cdot \sum_{k \in rows\ of\ \tilde{H}} |\tilde{H}_k^{(n)}|$$

In the expression above, C represents a constant, for example, the number of rows in the sum operation. An alternative would be to average a power of the absolute values, for example the square of the absolute values. Another alternative is to give different weights to different rows of $\tilde{H}^{(n)}$. Typically, rows are chosen which correspond to the most recently captured images.

An alternative method would be to use the component directly with no multiplication by U:

$$image^{(n)} = D(n,n) \cdot \tilde{V}_n^H$$

Multiplication by U provides the temporal information about the contribution of a component.

It is useful to associate each non-zero coordinate to a component. Association may be, for example, "hard" association, which means that it is associated with a single component, or "soft" association, which means assigning a probability that a coordinate is associated with a component.

Hard association may be formulated as follows: Coordinate i is associated with component n which maximizes the image at this coordinate.

$$component_i = \underset{n}{\arg\max}\{image_i^{(n)}\}$$

Soft association can be formulated as follows:

$$Pr\{component_i = n\} = \frac{image_i^{(n)}}{\sum_m image_i^{(m)}}$$

Soft association tends to assist with clustering as performed in step 120. However, the association step is not mandatory. It can be skipped.

Clustering

It will be appreciated that the position of the seats and the walls of the cabin are known. These fixed elements are background and may be removed. After removal of the background, the signals represent the occupants.

The purpose of clustering is to split the non-zero coordinates among occupants of the vehicle. This may be achieved by simply clustering the coordinates using standard clustering algorithms. An alternative approach is to make use of the a priori knowledge that different coordinates are associated with different components as shown in FIG. 5, where different coordinates are associated with different SVD (singular value decomposition) components by a hard association. For clarity, each component has a different color in the image.

Different occupants in a vehicle are expected to be separated into different SVD components, because they move differently in time. However, it is possible that a single SVD component will be associated with different occupants. In this case some of the coordinates within a component will form one cluster and others will form another cluster. Applying a clustering algorithm can be used to split this component into clusters.

Figure 14:
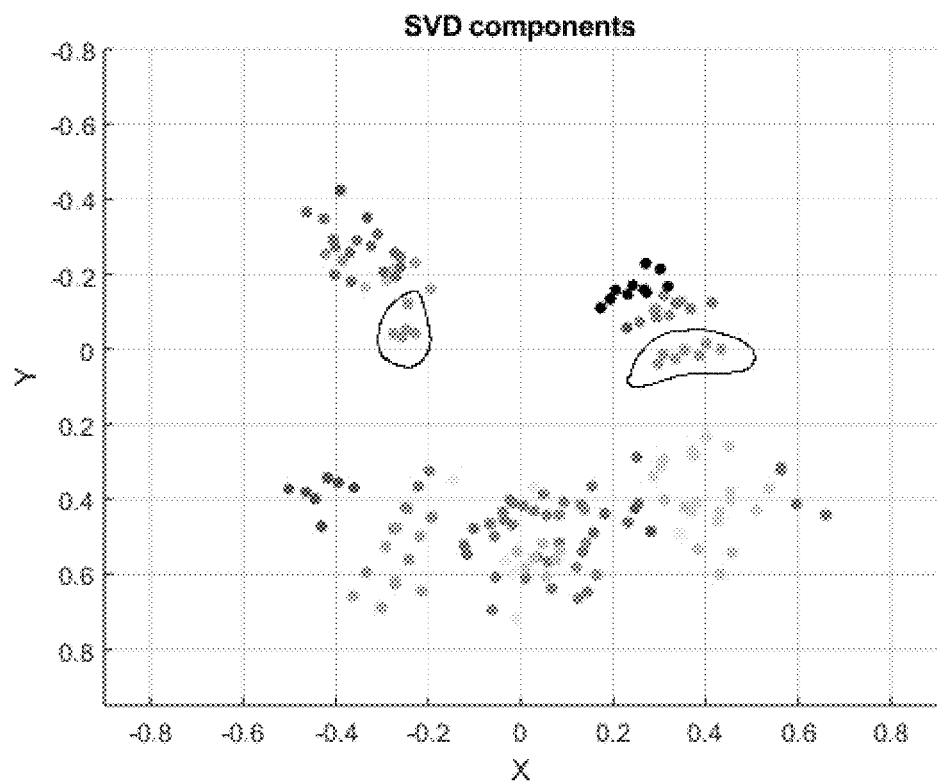
FIG. 14 is a two dimensional mapping of the area around a central radar sensor, showing SVD components.
Figure 15:
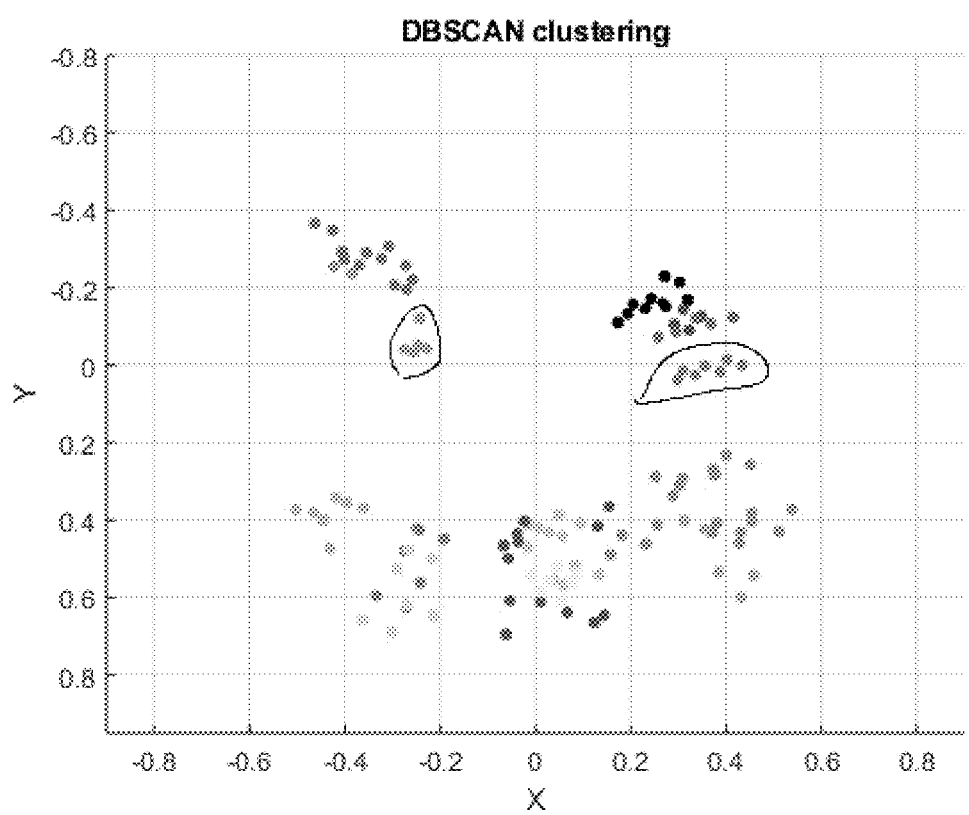
FIG. 15 shows the two dimensional mapping of the area around a central radar sensor after performing a DBSCAN clustering.

In FIG. 14, two set of coordinates associated with the same SVD component were circled. Application of clustering per SVD component generates FIG. 15, in which the circled clusters have been split to two components (different colors). FIG. 15 demonstrates per-component clustering using the DBSCAN algorithm, which also enables removing outliers. However, other clustering algorithms of the art may be used.

Referring back to FIG. 13, two methods of filtering were described. Method 1 involved dividing the image into high energy blobs and maintaining only the blob with the highest energy. In contradistinction, method 2 maintained only coordinates with energy above a threshold which could be relative to a peak value or an absolute value.

Clustering using the DBSCAN algorithm is only necessary with the method 2, as method 1 leaves only one cluster per component.

Now, clustering may be applied to the clusters themselves. Each cluster is represented as a Gaussian distribution with mean and covariance which fit the distribution of points within the cluster. Distance metrics may then be defined between these Gaussian distributions.

Figure 16:
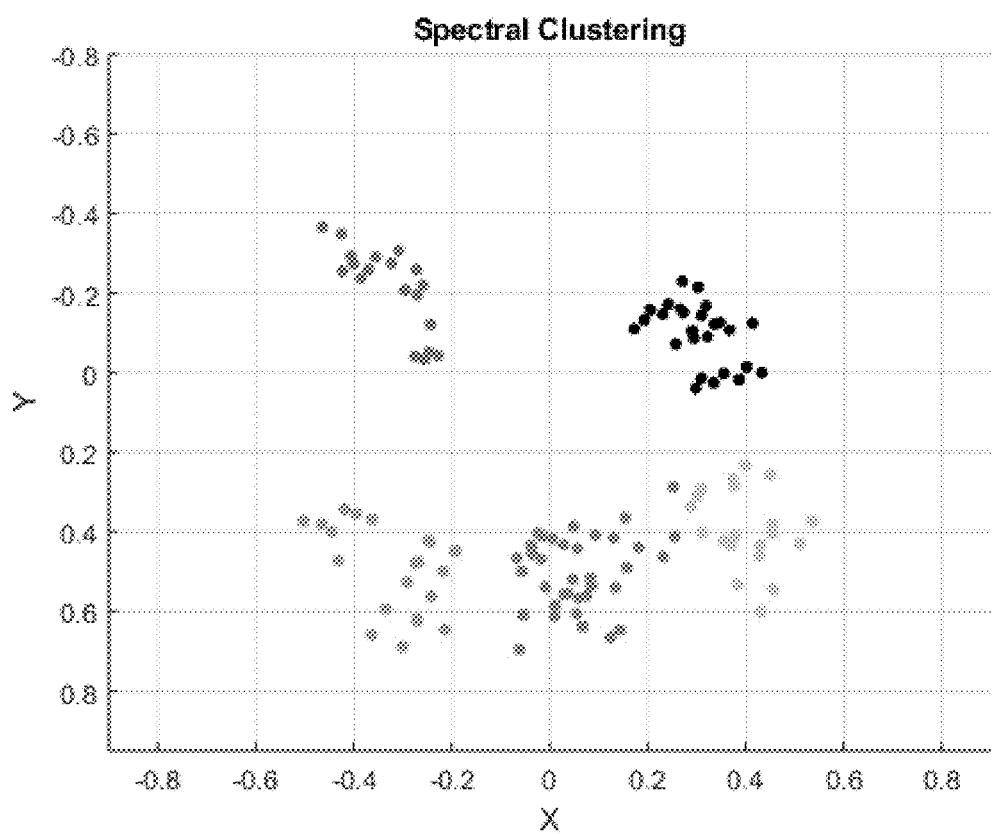
FIG. 16 shows the two dimensional mapping of the area around a central radar sensor after performing spectral clustering.

Distance between distributions can take many forms. For example, Kullback Leibler divergence, Bhattacharyya distance, Hellinger distance and L2-norm of the difference For example, spectral clustering which applies an algorithm known in the art, can be used to generate the results shown in FIG. 16, where five clusters are determined.

Fitting a Gaussian distribution to a collection of coordinates with given intensities can be done, for example, using the following equations. The notations are as follows.

The coordinates of a point in a cluster may be denoted by a column vector $\underline{r}=(r_x, r_y, r_z)^T$. However, these coordinates are not necessarily Cartesian, and not necessarily three-dimensional. Every point in a cluster is associated with a magnitude, denoted by m. Magnitudes of cluster points are real and positive, that is $m_i > 0$ for every point i.

A relative weight for each point in the cluster is defined, for example, by:

$$w_i = \frac{m_i}{\sum_i m_i}$$

The center of the cluster is simply:

$$\underline{\mu} = \sum_i w_i \cdot \underline{r}_i$$

A matrix is defined:

$$\tilde{c} = ((c_1)(c_2)(c_p))$$

where p denotes the number of points in a cluster, and $$\underline{c}_i = \sqrt{w_i} \cdot (\underline{r}_i - \underline{\mu})$$

The covariance of the cluster is defined as $$c = \tilde{c} \cdot \tilde{c}^T$$

Finally, a Gaussian distribution can be defined using the covariance matrix C and the center $\underline{\mu}$:

$$f_{Gauss}(\underline{x}) = \frac{1}{\sqrt{(2\pi)^k \cdot |c|}} \cdot e^{-\frac{1}{2}(\underline{x}-\underline{\mu})^T \cdot c^{-1} \cdot (\underline{x}-\underline{\mu})}$$

Other distributions may be used to describe a cluster of points, for example t-distribution, uniform distribution, Gaussian mixture, and so on.

Figure 17:
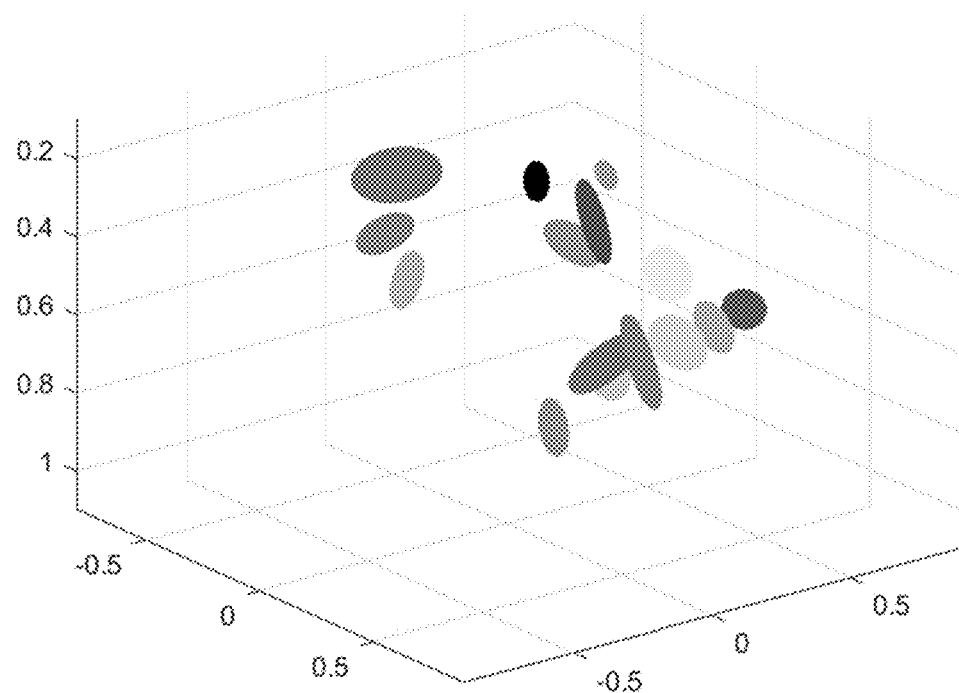
FIG. 17 represents clusters of points as Gaussians in a three-dimensional space.

FIG. 17 demonstrates representing clusters of points as Gaussians in a three-dimensional space.

It will be appreciated that each occupant of a vehicle may be associated with a seat. Seat association is the process of associating a seat in the vehicle to each occupant to determine whether a seat is occupied.

$$p_k(\underline{r}) = Pr\{\underline{r} \in seat_k\}$$

Figure 18:
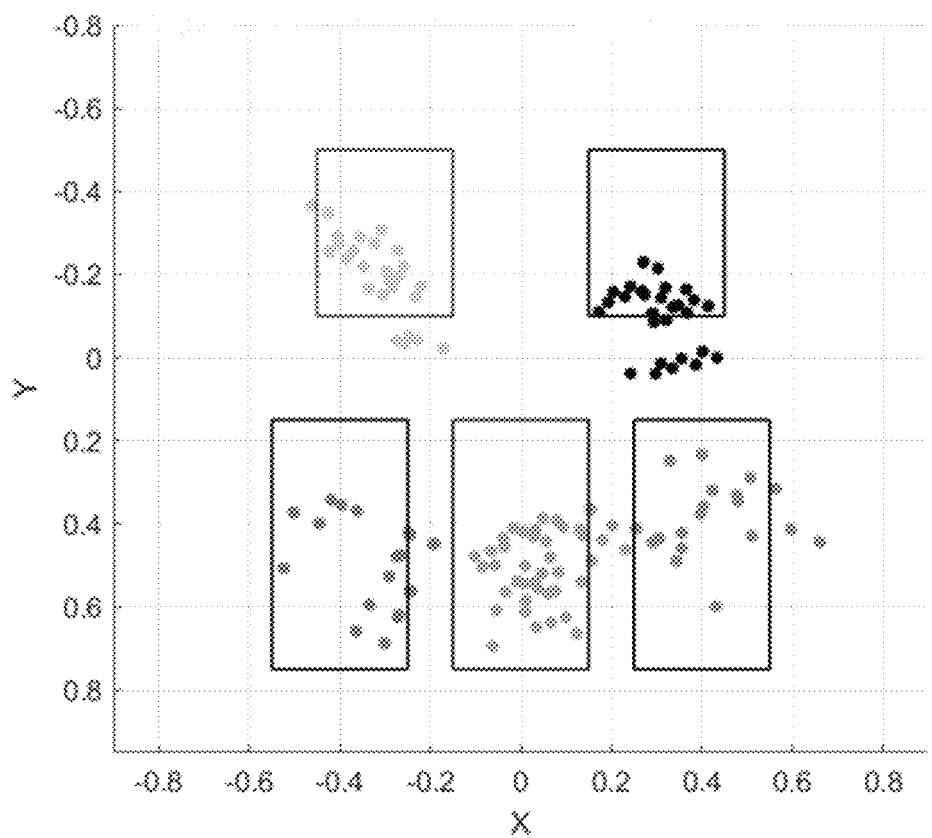
FIG. 18 shows the clusters that apparently represent different occupants with the position of the seats of the vehicle cabin superimposed thereover.

In FIG. 18, the rectangles define areas inside the vehicle associated with specific seats. Generally, the regions may be overlapping, and the distribution need not be uniform. However, as it is seen, the various clusters do align well with the boxes, and so it one can determine whether or not each seat is occupied.

$$t_k(cluster_q) = \prod_{\underline{r}_i \in cluster_q} \left( \frac{p_k(\underline{r}_i)}{\sum_{k'} p_{k'}(\underline{r}_i)} \right)$$

$$p_k(cluster_q) = \frac{t_k(cluster_q)}{\sum_{k'} t_{k'}(cluster_q)}$$

In the second distance metrics may be used as described earlier in the chapter about clustering.

$$d_k(cluster_q) = \text{distance from distribution of cluster } q \text{ to } p_k(r).$$

$$p_k(cluster_q) = \frac{e^{-d_k(cluster_q)}}{\sum_{k'} e^{d_{k'}(cluster_q)}}$$

Once the probability that cluster q is associated with seat k are determined for every pair {k, q} each cluster (q) can be associated with the seat (k) for which $p_k$ (cluster$_q$) is maximal.

We distinguish between "hard" occupancy and "soft" occupancy. We shall now describe how occupancy is calculated.

For "hard" occupancy the following rules are used:

Seats with no clusters associated to them are considered empty seats.

Seats with at least one cluster associated to them are considered occupied.

For "soft" occupancy the following expression can be used for the probability that seat k is occupied as a function of the probability matrix $p_k$(cluster$_q$) between each cluster q and each seat k':

$$Pr\{Seat_k \text{ is occupied}\} = 1 - Pr\{Seat_k \text{ is empty}\} = 1 - \prod_q (1 - p_k(cluster_q))$$

Figure 19:
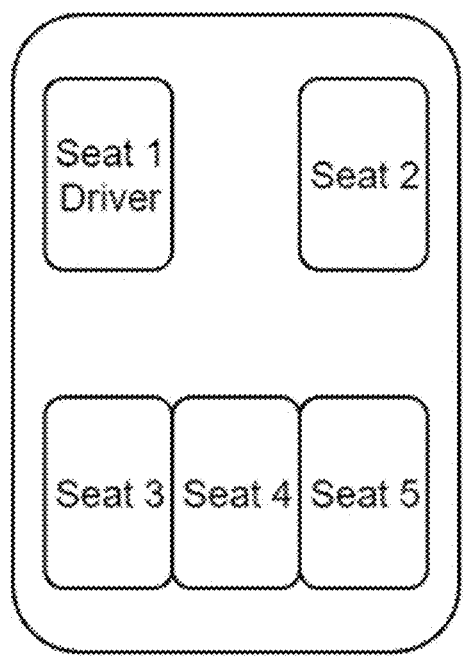
FIG. 19 shows seat arrangements shows the arrangement of the seats corresponding to that of FIG. 9.
Figure 20:
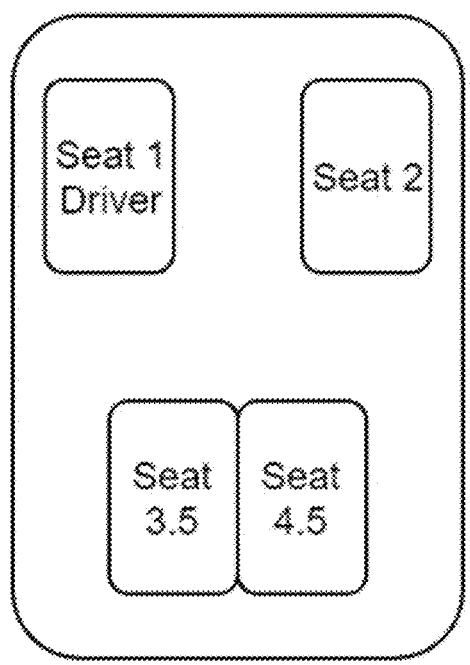
FIG. 20 shows intermediate positions between seats 3 and 4 and between seats 5 and 6.

As an example of a model for valid transitions within a vehicle, consider a vehicle with 2 rows. In the front row in seat 1 is a driver, and beside him is seat 2. In the second row are seats 3, 4 and 5, where seat 3 is behind the driver. We may also define positions between two seats, such as seat 3.5 and seat 4.5. These arrangements are demonstrated in FIGS. 19 and 20.

Figure 21:
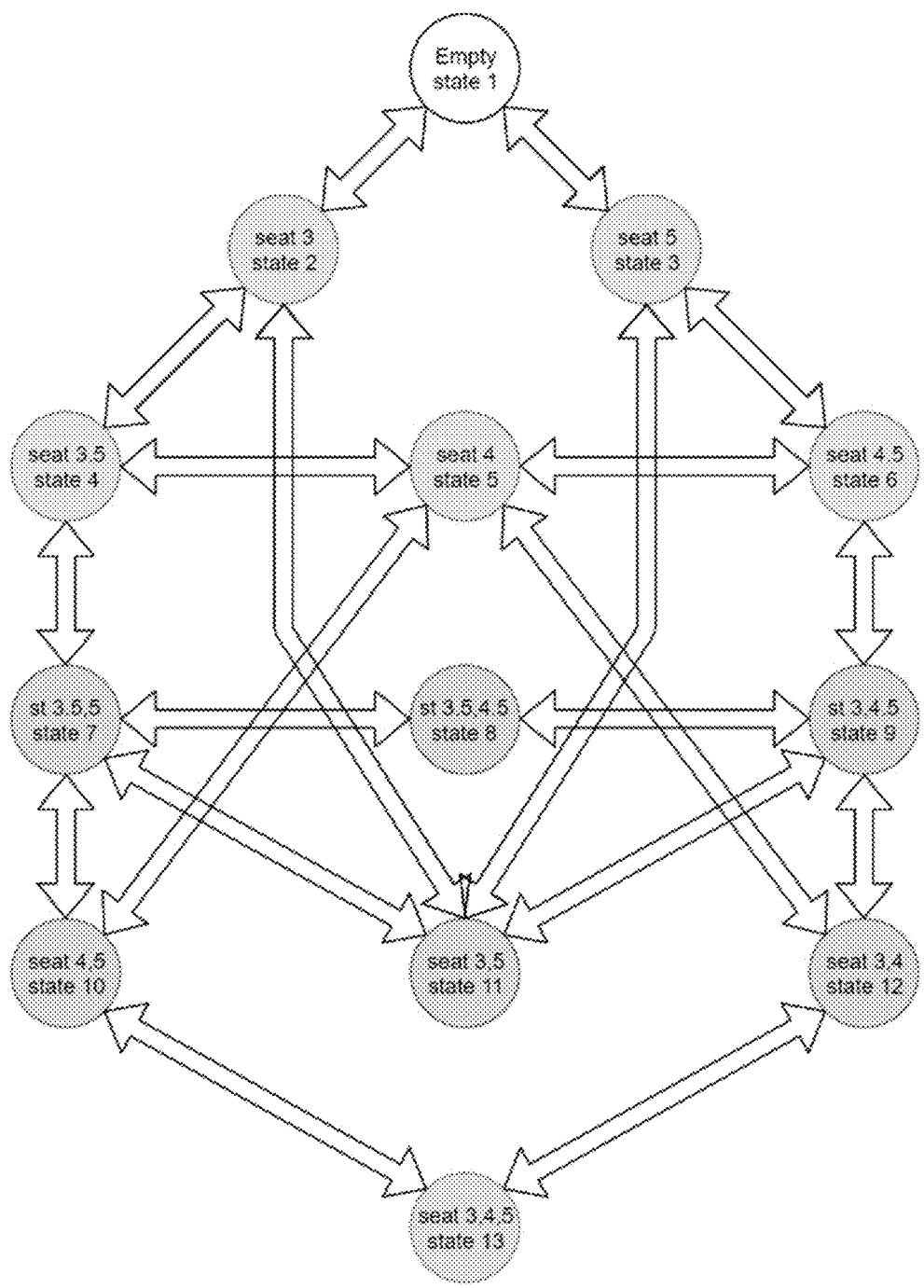
FIG. 21 is a transition model, showing valid state transitions between the back seats of the vehicle.

FIG. 21 demonstrates an occupancy transition diagram for the second row of FIG. 10. Each circle indicates an occupancy state, where the occupied seats and state number are indicated on the circle.

The occupancy probabilities Pr{Seat$_k$ is occupied} may be combined with the transition model in the following way.

A transition probability is assigned to each of the transitions in the diagram. For example for state 1, there is a probability of transition to state 2, a probability of transition to state 3, and a probability of remaining in state 1. These probabilities can be defined arbitrarily, or can be based on statistics. Wherever there is no connection between states in the diagram, it is assumed that the transition probability is 0. For example, the probability of transition from state 1 to state 5 is 0.)

The transition probability from state $s_1$ to state $s_2$ is denoted by $p_t(s_1, s_2)$.

Each state s has occupied seats associated with it. The occupied seats associated with state s is denoted by $o_s$. For example state 4 has seats 3 and 5 occupied: $o_4=\{3,5\}$ Updating the probability of the system being in states can be done as follows:

$$p_s = \prod_{i \in o_s} Pr\{\text{seat } i \text{ is occupied}\} \cdot$$

$$\prod_{i \notin o_s}(1 - Pr\{\text{seat } i \text{ is occupied}\}) \cdot \sum_{s'} p_{s'} p_t(s', s)$$

In words, the probability of the occupancy being in state s is updated to the probability that the seats fit state s multiplied by the sum of transition probabilities to state s from states s' multiplied by the probability of occupancy being in these states.

In some embodiments the exact probabilities are not calculated, but rather a number which is proportional to the probabilities.

In some embodiments the sum $$\sum_{s'} p_{s'} p_t(s', s)$$

may be replaced by a single term which represents the most likelihood transition to state s as follows:

$$p_s \approx \prod_{i \in o_s} Pr\{\text{seat } i \text{ is occupied}\} \cdot$$

$$\prod_{i \notin o_s}(1 - Pr\{\text{seat } i \text{ is occupied}\}) \cdot \max_{s'}\{p_s, p_t(s', s)\}$$

In some embodiments the logarithm of the probabilities is used, and the multiplications above may be replaced by sums as follows:

$$\log\{p_s\} \approx \sum_{i \in o_s} \log(Pr\{\text{seat } i \text{ is occupied}\}) +$$

$$\sum_{i \notin o_s} \log(1 - Pr\{\text{seat } i \text{ is occupied}\}) + \log\left(\max_{s'}\{p_{s'} p_t(s', s)\}\right)$$

In some embodiments, the most likely state may be selected, and a few steps traced back according to the most likely consecutive states leading to it. Indicating a previous state that lead to the most likely current state stabilizes the system by reducing sensitivity to errors in the seat occupation probabilities.

Implementation of the last equation lends itself to linear programming methods.

Figure 22:
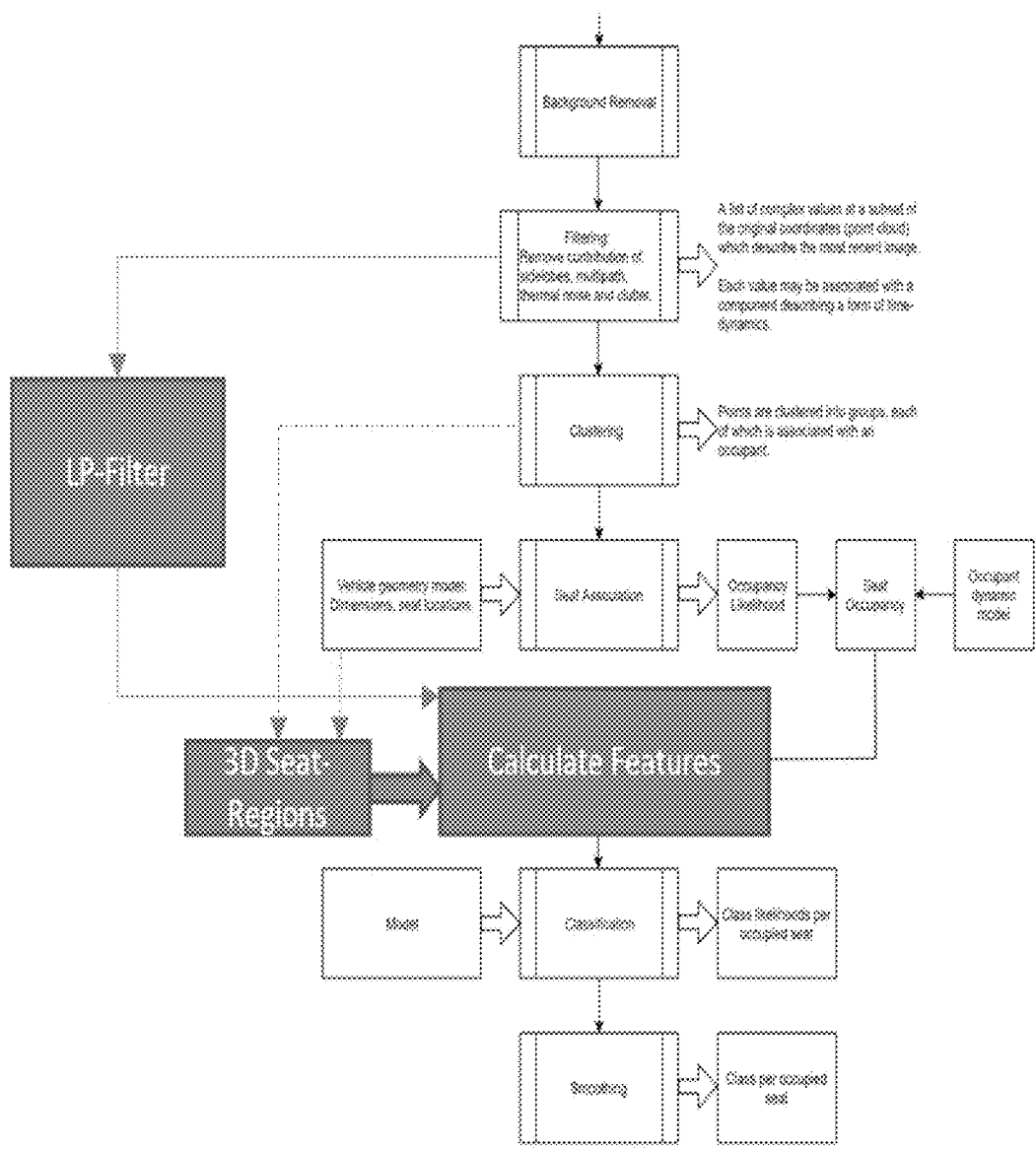
FIG. 22 is a flowchart showing how occupants may be classified.

With reference to FIG. 22, for the Occupant Classification, where required, a LP (low pass) filter may optionally be applied on the filtered 3D-Image for a configurable time constant (typically a few seconds). The LP filter may be a moving average or may be an IIR (infinite impulse response) exponential moving average filter. In other configurations, no low pass filter may be applied.

Use of an LP filter tends to maintain useful volumetric information (preserving voxels that account for reflections of the body). Different body parts may move at different times, and an LP filter may facilitate accumulating the information over time, giving a single 3D image.

The image is then divided into 3D regions, where each region encloses a single subject.

In the case of a vehicle, knowing its size and geometry, some measurements of the vehicle cabin can be utilized to derive the 3D regions.

For example for a 5 seat car, the following measurements are constant per car model relative to the sensor origin, and can be collected:
FRF—Front row seat foremost position (measured referring to seat "center of mass"—see image)
FRR—front row seat rearmost position (measured referring to seat "center of mass"—see image)
RRC—Rear row bench "center of mass"
BNCW—Rear row bench width
STH—seat height from ground to edge
SSH—Sensor height from ground to sensor Another option is to use the decision of an upper layer that derives the number of occupants and the location (providing [x,y] coordinates for each occupant, and opening a box around that location [x−dx, x+dx, y−dy, y+dy, 0, SSH]).

Yet another option is to use the SVD decomposition to "color" each voxel by component number giving an initial guess for the clustering of voxels. Then each component can be put through DBSCAN—Density Based Spatial Classification of Applications with Noise (geometric) clustering to remove outliers and separate geometrically independent clusters to separate components. From this step on, each component (cluster) can no longer be separated and additional clustering is done to separate into cluster groups Per 3D region, volumetric and intensity based features may be extracted.

Hand crafted cluster features may be utilized to assess the identity of an occupant.

Notation:

Given a 3D image region, all voxels that have an intensity above a certain level are extracted. This gives a list of the occupied voxels of the 3D Region.

$$voxel_i = [x_i, y_i, z_i, I_i], i=1 \ldots N$$

$$PC = \{voxel_1 \ldots voxel_N\}$$

From this list of points the following features are calculated. The coordinates are relative to a defined center-point of the 3D-Region. In the case of a car-seat, the center-point is defined to be directly on the seat (z-coordinate) and in the region where an adult's center of intensity is expected to be (x-, y-coordinate).

Number of Occupied Voxels

The number of occupied voxels may indicate the volume of the region that is occupied.

Number of occupied voxels=$N$

Center of Intensity

The center of intensity is the average position of the voxels weighted by their intensity $$C = [C_x, C_y, C_z] = \frac{\Sigma_i(I_i \cdot [x_i, y_i, z_i])}{\Sigma_i I_i}$$

Covariance and Weighted Covariance

The covariance gives a measure of how the points are distributed in space. It the case of occupant-classification it indicates the posture of the person (e.g. leaning forward adult/baby in an infant-seat)

Figure 23:
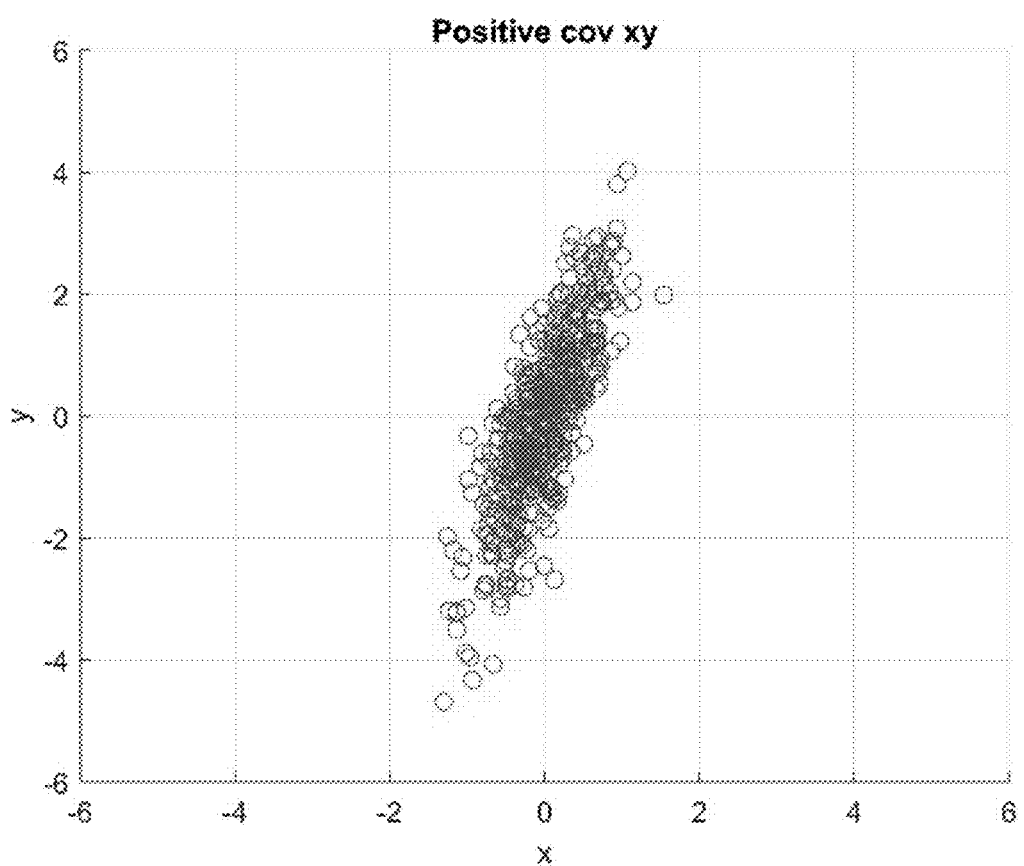
FIG. 23 shows a positive cov in the xy plane.
Figure 24:
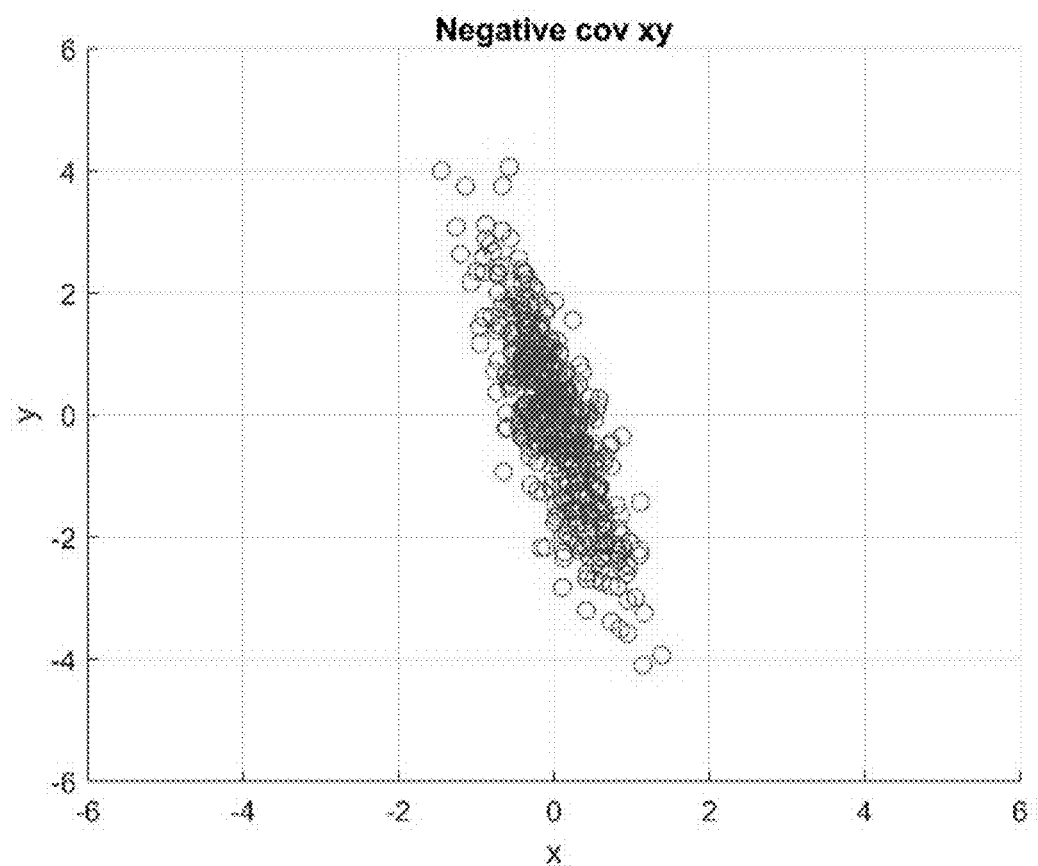
FIG. 24 shows a negative coy in the xy plane.

FIGS. 23 and 24 illustrate this principle.

The following algorithm shows an example of code for calculating weighted covariance.

*numDimensions* = 3;

gmm_paramsmean = zeros(*numDimensions*, 1);

-continued gmm_paramscov = zeros(*numDimensions*, *numDimensions*, 1);

weights = iSeat_pts_Intensity/ sum(iSeat_pts_Intensity);

gmm_paramsmean = sum(weights * iSeat_pts_XYZ)';

zero_mean_weighted_points = sqrt(weights). * (iSeat_pts_XYZ − gmm_paramsmean');

gmm_paramscov =

(zero_mean_weighted_points' * zero_mean_weighted_points);

$$weight_i = \frac{I_i}{\sum_{i=0}^{N} I_i}$$

$$zmwp_i = \sqrt{weight_i} \cdot ([x_i, y_i, z_i] - C)$$

$$cov = zmwp^T \cdot zmwp$$

Extrema of Coordinates in 3D-Region

The extreme (maximum/minimum) coordinates of all 3 Cartesian axes give a measure of the region that is occupied in the 3D-Region.

Figure 25:
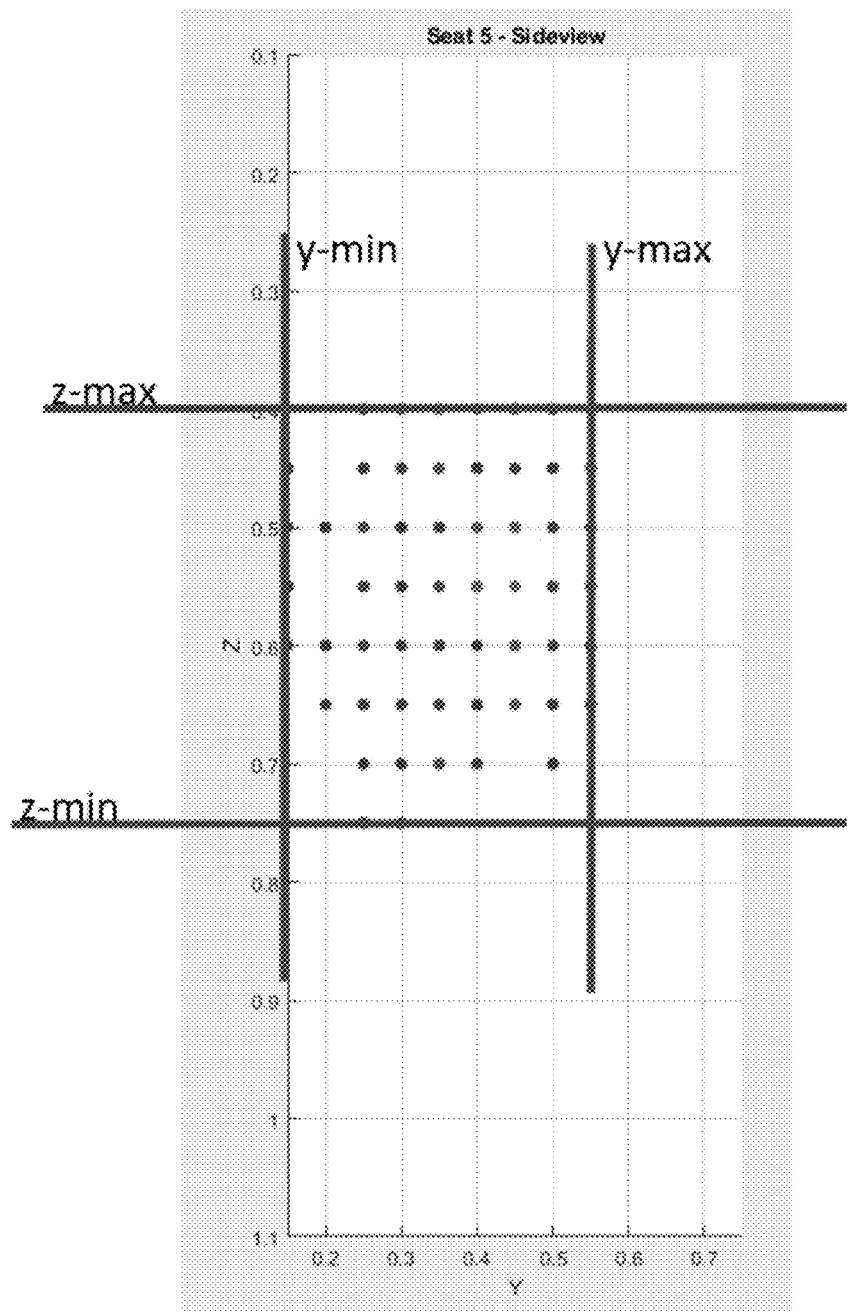
FIG. 25 is a side view of seat 5, showing the upper and lower boundaries and forward and rearward most boundaries of the cluster of signals interpreted as being the occupant.

With reference to FIG. 25, by drawing a rectangle around a cluster one can obtain an indication of size and shape of the occupant.

$$X_{min} = \min(X), X = x_1 \ldots x_N$$

$$X_{max} = \max(X), X = x_1 \ldots x_N$$

$$Y_{min} = \min(Y), Y = y_1 \ldots y_N$$

$$Y_{max} = \max(Y), Y = y_1 \ldots y_N$$

$$Z_{min} = \min(Z), Z = z_1 \ldots z_N$$

$$Z_{max} = \max(Z), Z = z_1 \ldots z_N$$

Center of Intensity for Defined Z-Value

For an adult, the center of intensity on z-slices over the seat height is typically close to the backrest of the seat, for an infant in a rearward-facing baby seat the center of mass in certain slices is typically shifted more to the front.

$$weight_i = \frac{I_i}{\sum_{i=0}^{N} I_i} \forall i \in \{1 \ldots N\} \text{ s.t. } z_i = \text{e.g. } 0.6 \text{ m over seat}$$

$$zmwp_i = \sqrt{weight_i} \cdot ([x_i, y_i, z_i] - C) \forall i \in \{1 \ldots N\} \text{ s.t. } z_i$$
$$= \text{e.g. } 0.6 \text{ m over seat}$$

$$cov = zmwp^T \cdot zmwp$$

Mean Intensity $$\bar{I} = \frac{1}{N} \sum_{i=1}^{N} I_i$$

Max Intensity $$I_{max} = \max(I), I = I_1 \ldots I_N$$

Energy Below the Seat Level

The energy below the seat level can indicate if an infant is on the seat. In case of an infant being on this seat there are no reflections from below the sitting height expected.

$$I_{belowseat} = \text{sum}(I_i) \forall i \in \{1 \ldots N\}, z_i > \text{seatheight}$$

To stabilize the classification output, the classification may be saved to a buffer of a few seconds and a majority vote or a stabilizer with hysteresis may be used to determine the final classification-decision.

It is appreciated that certain features of the invention, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments unless the embodiment is inoperative without those elements.

Although the invention has been described in conjunction with specific embodiments thereof, it is evident that other alternatives, modifications, variations and equivalents will be apparent to those skilled in the art. Accordingly, it is intended to embrace all such alternatives, modifications, variations and equivalents that fall within the spirit of the invention and the broad scope of the appended claims. Additionally, the various embodiments set forth hereinabove are described in terms of exemplary block diagrams, flow charts and other illustrations. As will be apparent to those of ordinary skill in the art, the illustrated embodiments and their various alternatives may be implemented without confinement to the illustrated examples. For example, a block diagram and the accompanying description should not be construed as mandating a particular architecture, layout or configuration.

In further embodiments, the processing unit may be a digital processing device including one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, an OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the system disclosed herein includes one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device.

In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media. In some embodiments, the system disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof. In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, the system disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the system disclosed herein includes one or more databases, or use of the same. In view of the disclosure provided herein, those of skill in the art will recognize that many databases are suitable for storage and retrieval of information as described herein. In various embodiments, suitable databases include, by way of non-limiting examples, relational databases, non-relational databases, object oriented databases, object databases, entity-relationship model databases, associative databases, and XML, databases. In some embodiments, a database is internet-based. In further embodiments, a database is web-based. In still further embodiments, a database is cloud computing-based. In other embodiments, a database is based on one or more local computer storage devices.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included. Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described. Methods of the present invention may be implemented by performing or completing manually, automatically, or a combination thereof, selected steps or tasks.

The descriptions, examples, methods and materials presented in the claims and the specification are not to be construed as limiting but rather as illustrative only. Meanings of technical and scientific terms used herein are to be commonly understood as by one of ordinary skill in the art to which the invention belongs, unless otherwise defined. The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for detecting occupants in a vehicle cabin comprising:
   for each of a plurality of times, using an array of transmitting and receiving elements to generate a set of complex values associated with voxels having coordinates within the vehicle cabin;
   converting each set of complex values into a 3D complex image representing multiple seats within the vehicle cabin;
   clustering the coordinates of the voxels in the 3D complex image representing multiple seats within the vehicle cabin into one or more clusters;
   associating each cluster with a different seat in the vehicle;
   analyzing the clusters to determine presence of one or more occupants inside the vehicle; and
   using geometrical data of the vehicle regarding the position of the different seats to determine which seats in the vehicle are occupied.

2. The method according to claim 1 wherein the array of transmitting and receiving elements are radar imaging or ultrasonic imaging elements.

3. The method according to claim 1 wherein the array of transmitting and receiving elements utilizes radiation having a wavelength from 0.1 cm to 10 cm.

4. The method according to claim 1 further comprising a step of background removal prior to the step of clustering.

5. The method according to claim 1 further comprising a step of filtering one or more images prior to the step of clustering.

6. The method according to claim 5 wherein if the filtering step leaves components as associated with at least two separate clusters, using the DBSCAN algorithm to associate components with a single cluster.

7. The method of claim 1 wherein a clustering algorithm is applied to each cluster which is represented as a Gaussian distribution with mean and covariance which fit the distribution of points within the cluster and applying distance metrics between the Gaussian distributions.

8. The method of claim 7 when the distance metric between Gaussian distributions utilizes at least one of Kullback Leibler divergence, Bhattacharyya distance, Hellinger distance and L2-norm of the difference.

9. The method of claim 7 wherein a spectral clustering algorithm is used to determine distance between different distributions.

10. The method of claim 1 wherein a cluster of points is defined by a technique selected from t-distribution, uniform distribution or a Gaussian mixture.

11. The method of claim 1, wherein extreme voxels of a cluster determine a box around an occupant that may be used to categorize the occupant.

12. The method of claim 11 wherein the relative position of a center of intensity of a cluster of voxels with respect to a seat back is used as an indication that an occupant is leaning forwards or backwards.

13. The method of claim 1 wherein a cluster lacking voxels below seat level are indicative of an infant.

14. A system for classifying one or more occupants in a vehicle cabin comprising at least one seat, the system comprising:
- at least one transmitter configured to transmit a plurality of Radio Frequency (RF) signals;
- at least one electromagnetic sensor connected to said at least transmitter, wherein said at least one electromagnetic sensor is configured to provide RF response data;
- a Radio Frequency Signals Measurement Unit (RFSMU) configured to receive said RF responses and measure said RF responses; and
- a processor connected to said sensor, said processor configured and operable to:
- generate at least one 3D (three dimensional) complex image representing multiple seats within the vehicle cabin based on said RF responses;
- process one or more consecutive 3D images of said obtained 3D complex images representing multiple seats within the vehicle cabin, by removing a background from 3D images;
- filter the 3D complex images representing multiple seats within the vehicle cabin images by removing contribution of at least one of sidelobes, multipath, thermal noise and clutter;
- cluster coordinates of voxels in said filtered 3D complex images representing multiple seats within the vehicle cabin;
- associate each cluster of voxels in said filtered 3D complex images with a different seat within the vehicle cabin;
- analyze the clusters to determine presence of one or more occupants inside the vehicle; and
- classify the one or more occupants based on distribution of points for each cluster in said 3D complex images representing multiple seats within the vehicle cabin and according to said vehicle geometry.

15. A method for classifying one or more occupants in a vehicle cabin comprising at least one seat, the method comprising:
- obtaining at least one 3D (three dimensional) complex image representing multiple seats within the vehicle cabin;
- processing at least one of said obtained 3D complex images representing multiple seats within the vehicle cabin, by:
- removing a background from 3D complex images representing multiple seats within the vehicle cabin,
- filtering the 3D complex images representing multiple seats within the vehicle cabin by removing contribution of at least one of sidelobes, multipath, thermal noise and clutter, and
- clustering coordinates of voxels in filtered 3D complex images representing multiple seats within the vehicle cabin;
- associating at least one seat with at least one occupant; and
- classifying the one or more occupants based on distribution of points for each cluster in said 3D complex images representing multiple seats within the vehicle cabin and according to said vehicle geometry.

16. The method of claim 15 wherein the step of classifying the occupants further includes class likelihoods per occupied seat.

17. The method of claim 16 wherein the step of classifying the occupants further comprises a smoothing process.

18. The method of claim 17 further comprising monitoring physiological data of at least one occupant of the vehicle.

19. The method of claim 18 wherein the physiological data is selected from at least one of breathing rate, heart rate, heart rate variability and combinations thereof.

20. The method of claim 17 further comprising assessing the occupant's mental condition based upon the physiological data.

* * * * *